United States Patent
Groetzbach et al.

(10) Patent No.: US 12,161,849 B2
(45) Date of Patent: *Dec. 10, 2024

(54) INJECTION DEVICE WITH OUTER CAP WITH NEEDLE PROTECTION CAP REMOVAL ELEMENT AND METHOD FOR ASSEMBLING AN INJECTION DEVICE

(71) Applicant: Ypsomed AG, Burgdorf (CH)

(72) Inventors: Felix Groetzbach, Gerlafingen (CH); Markus Tschirren, Burgdorf (CH); Stefan Burren, Schwarzenburg (CH); Urs Kloetzli, Burgdorf (CH); Peter Stettler, Ersigen (CH); Benjamin Loretz, Solothurn (CH)

(73) Assignee: Ypsomed AG, Burgdorf (CH)

( * ) Notice: Subject to any disclaimer, the term of this patent is extended or adjusted under 35 U.S.C. 154(b) by 134 days.

This patent is subject to a terminal disclaimer.

(21) Appl. No.: 17/559,777

(22) Filed: Dec. 22, 2021

(65) Prior Publication Data

US 2022/0111154 A1    Apr. 14, 2022

Related U.S. Application Data

(63) Continuation of application No. 16/259,797, filed on Jan. 28, 2019, now Pat. No. 11,311,681, which is a
(Continued)

(30) Foreign Application Priority Data

Jul. 28, 2016   (CH) ..................................... 00989/16
Sep. 8, 2016   (CH) ..................................... 01166/16

(51) Int. Cl.
*A61M 5/32*   (2006.01)
*A61M 5/20*   (2006.01)
*A61M 5/24*   (2006.01)

(52) U.S. Cl.
CPC ........ *A61M 5/3204* (2013.01); *A61M 5/3202* (2013.01); *A61M 5/326* (2013.01);
(Continued)

(58) Field of Classification Search
CPC .............. A61M 5/3204; A61M 5/3202; A61M 5/3213; A61M 2207/00; A61M 2207/10; A61M 2005/3215
(Continued)

(56) References Cited

U.S. PATENT DOCUMENTS 9,339,610 B2    5/2016  Julian et al.
2010/0016795 A1  1/2010  Mcloughlin
(Continued)

FOREIGN PATENT DOCUMENTS

EP     2878321 A1    6/2015
EP     2878322 A1    6/2015
(Continued)

OTHER PUBLICATIONS

PCT, "International Preliminary Report on Patentability", Application No. PCT/CH2017/000074, Jan. 29, 2019, 16 pages.
(Continued)

*Primary Examiner* — Nathan R Price
*Assistant Examiner* — Anna E Goldberg-Richmeier
(74) *Attorney, Agent, or Firm* — Dorsey & Whitney LLP

(57) ABSTRACT

An injection device comprising a cap for removing a needle protection cap from a product container, and a method for assembling an injection device. The cap comprises an engaging element for removing the needle protection cap from the product container when the cap is removed from the injection device. The engaging element can be deformed in such a way that the engaging element can be moved from a distanced position, in which the engaging element is radially distanced from the needle protection cap, into an
(Continued)

engagement position, in which the engaging element engages with the needle protection cap, with the engaging element being deformed when the cap is removed.

18 Claims, 19 Drawing Sheets

Related U.S. Application Data continuation of application No. PCT/CH2017/000074, filed on Jul. 26, 2017.

(52) U.S. Cl.
CPC .............. *A61M 5/20* (2013.01); *A61M 5/2033* (2013.01); *A61M 5/24* (2013.01); *A61M 5/3243* (2013.01); *A61M 2005/3247* (2013.01); *A61M 2205/273* (2013.01)

(58) Field of Classification Search
USPC .......................................................... 604/198
See application file for complete search history.

(56) References Cited

U.S. PATENT DOCUMENTS

| | | |
|---|---|---|
| 2012/0203186 A1 | 8/2012 | Vogt et al. |
| 2014/0257192 A1* | 9/2014 | Morgan .............. A61M 5/3202 604/189 |
| 2016/0243315 A1* | 8/2016 | Perche ................ A61M 5/3204 |
| 2016/0354551 A1 | 12/2016 | Keim et al. |
| 2017/0014578 A1* | 1/2017 | Bunch ................ A61M 5/3202 |
| 2017/0259009 A1 | 9/2017 | Sjökvist |
| 2017/0354789 A1* | 12/2017 | Bendek .............. A61M 5/3204 |
| 2018/0133407 A1 | 5/2018 | Kemp et al. |
| 2019/0151565 A1 | 5/2019 | Groetzbach et al. |
| 2019/0201634 A1* | 7/2019 | Newton .............. A61M 5/3213 |

FOREIGN PATENT DOCUMENTS

| | | |
|---|---|---|
| EP | 2923716 A1 | 9/2015 |
| FR | 3011186 A1 | 4/2015 |
| WO | 2010136076 A1 | 12/2010 |
| WO | 2015144871 A1 | 10/2015 |
| WO | 2018018167 A1 | 2/2018 |

OTHER PUBLICATIONS

PCT, "International Search Report", Application No. PCT/CH2017/000074, Oct. 23, 2017, 7 pages.

* cited by examiner

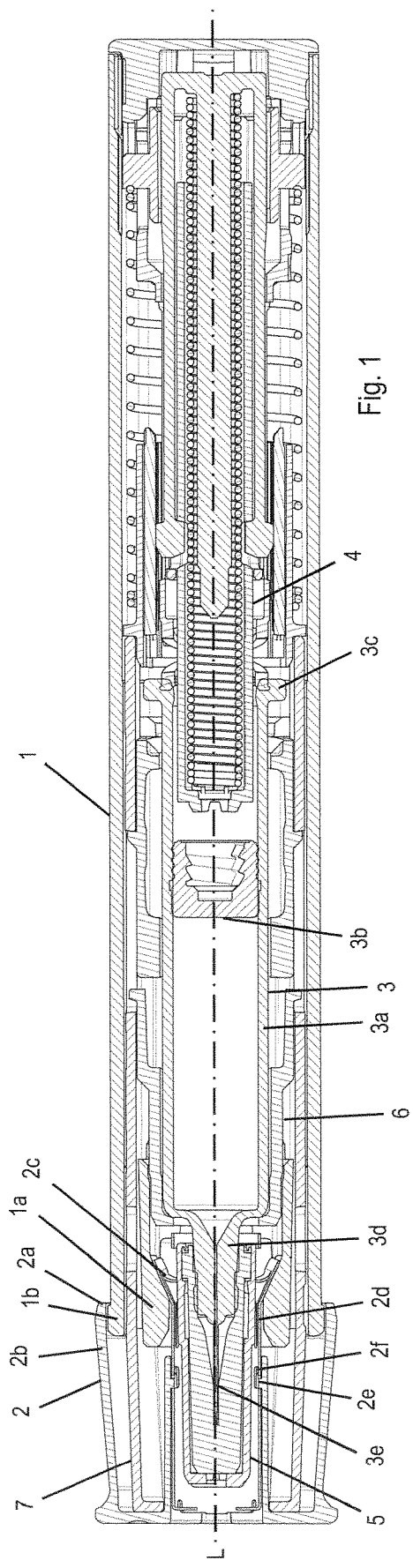
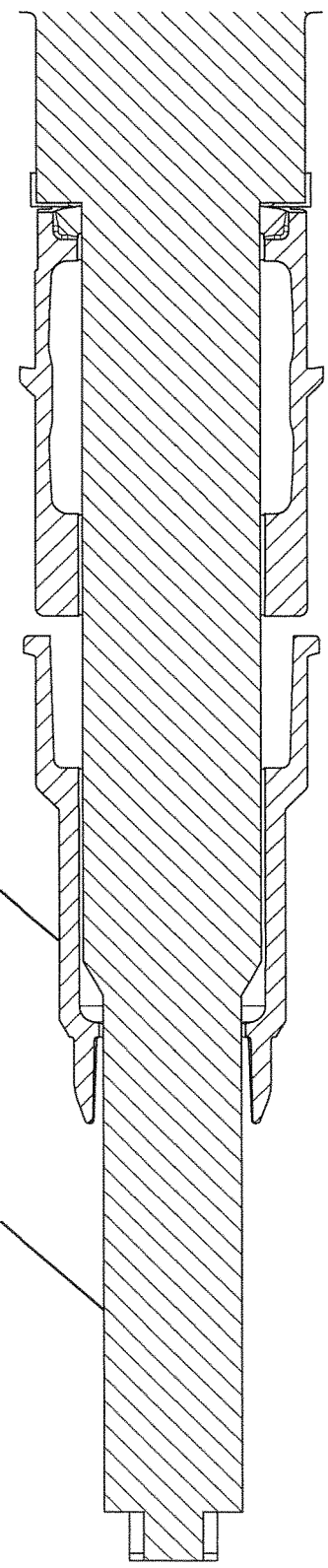
Fig. 1
Fig. 2a

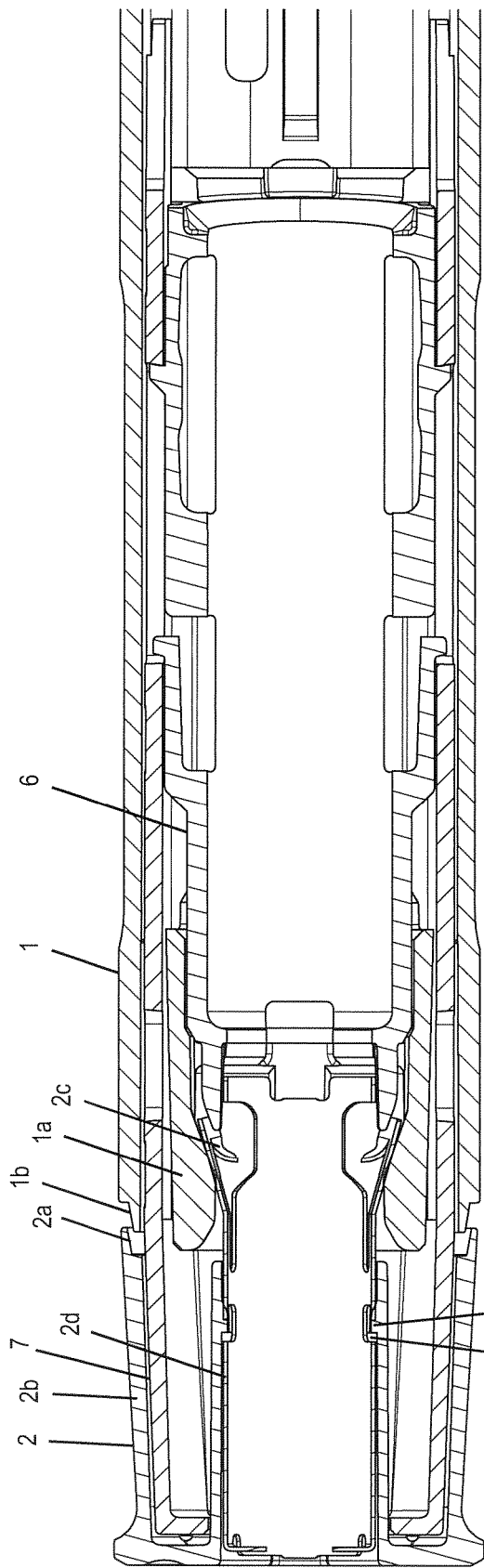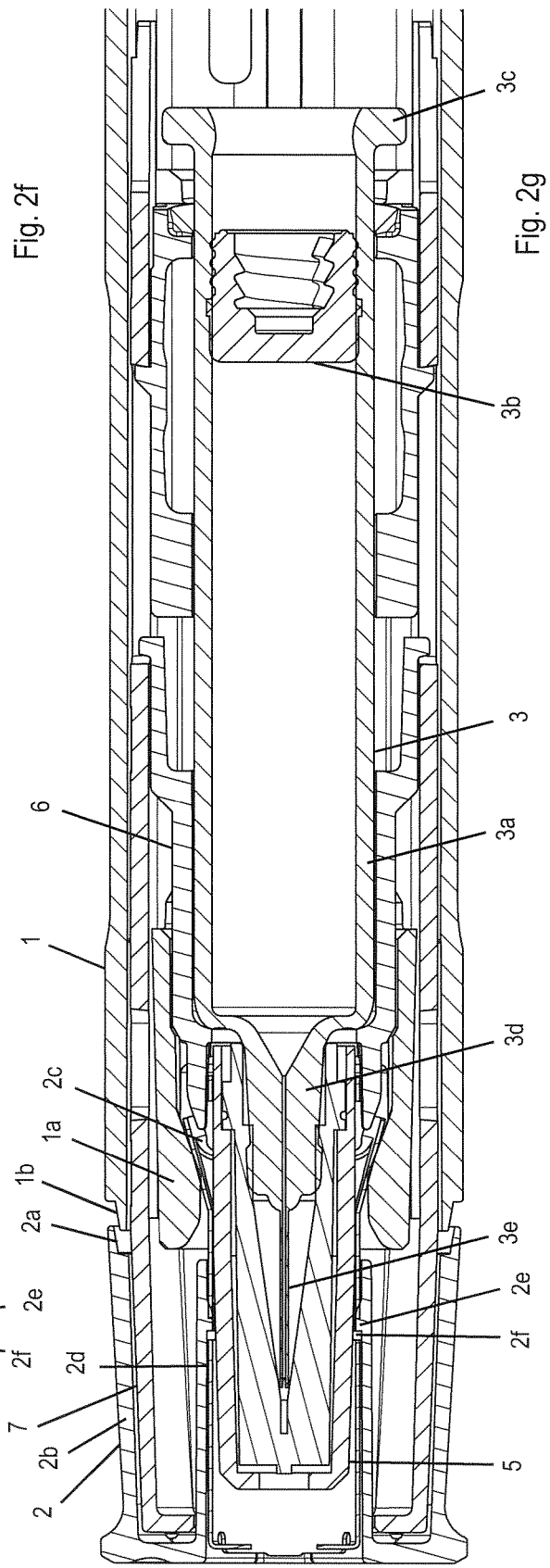

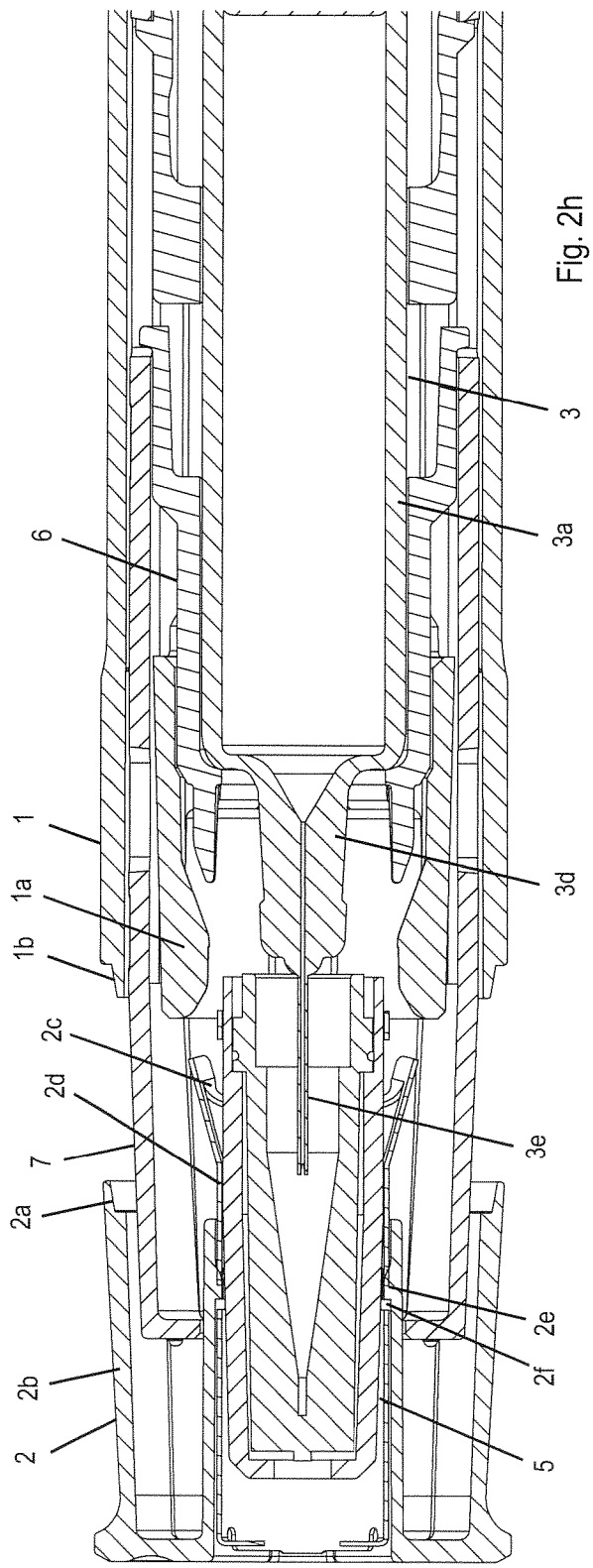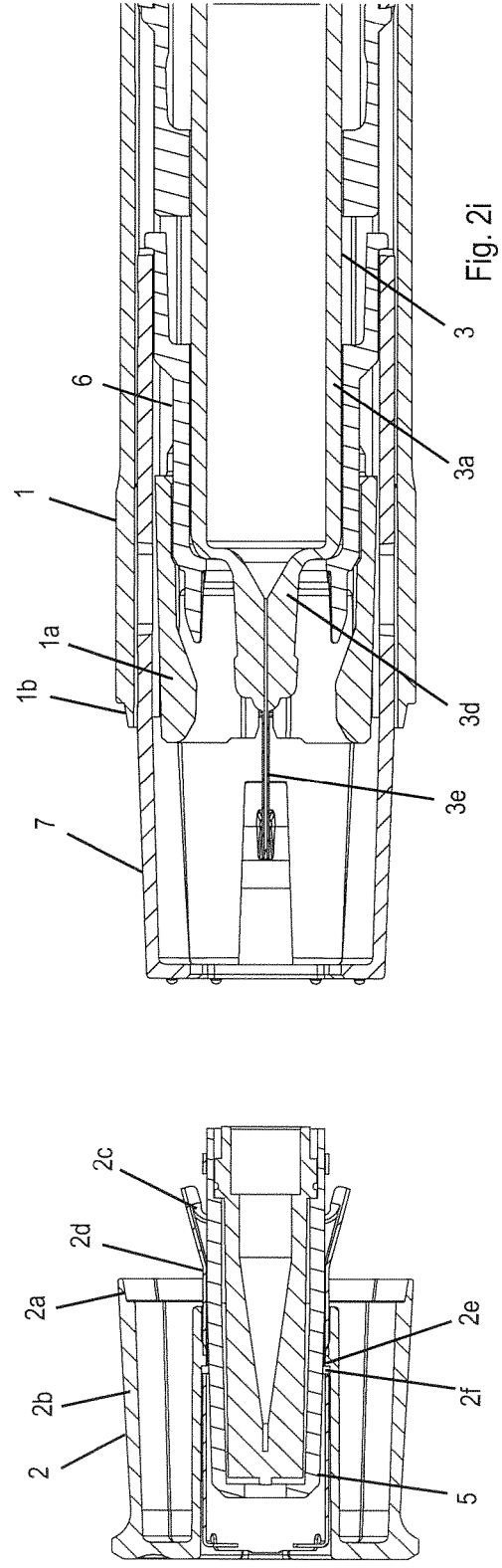

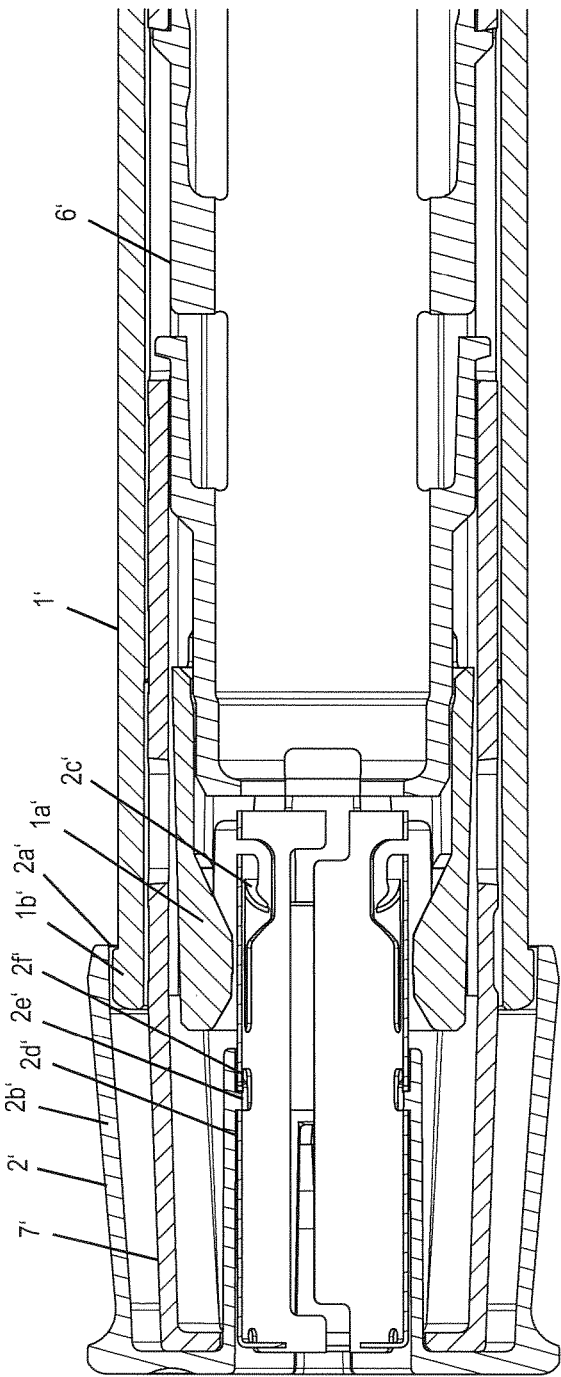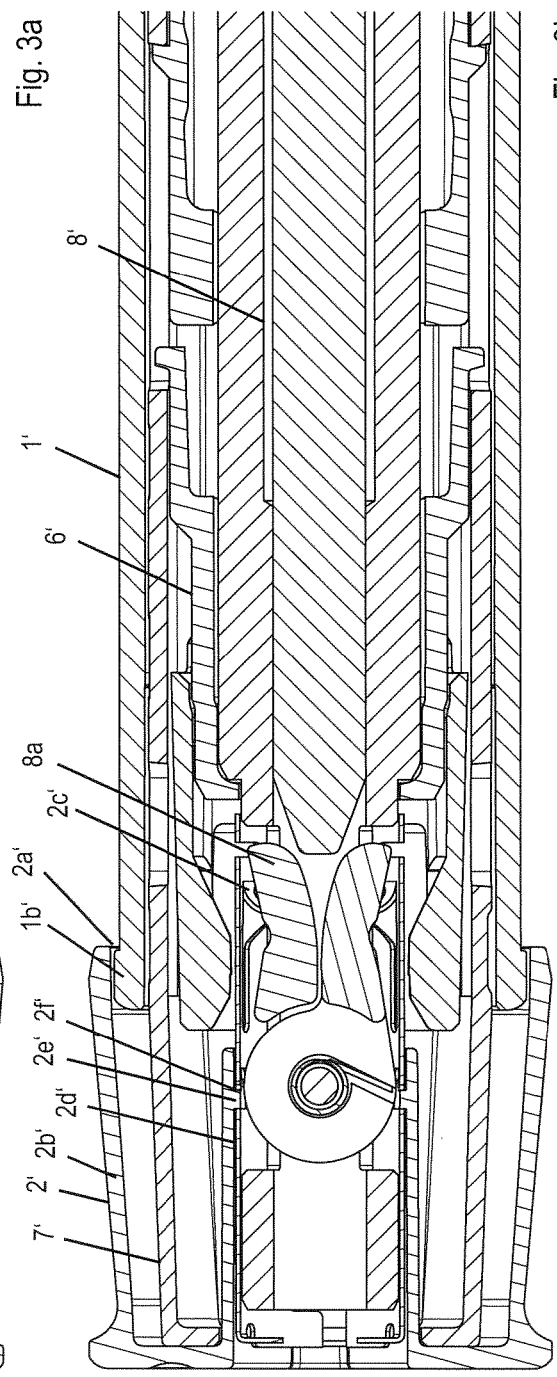

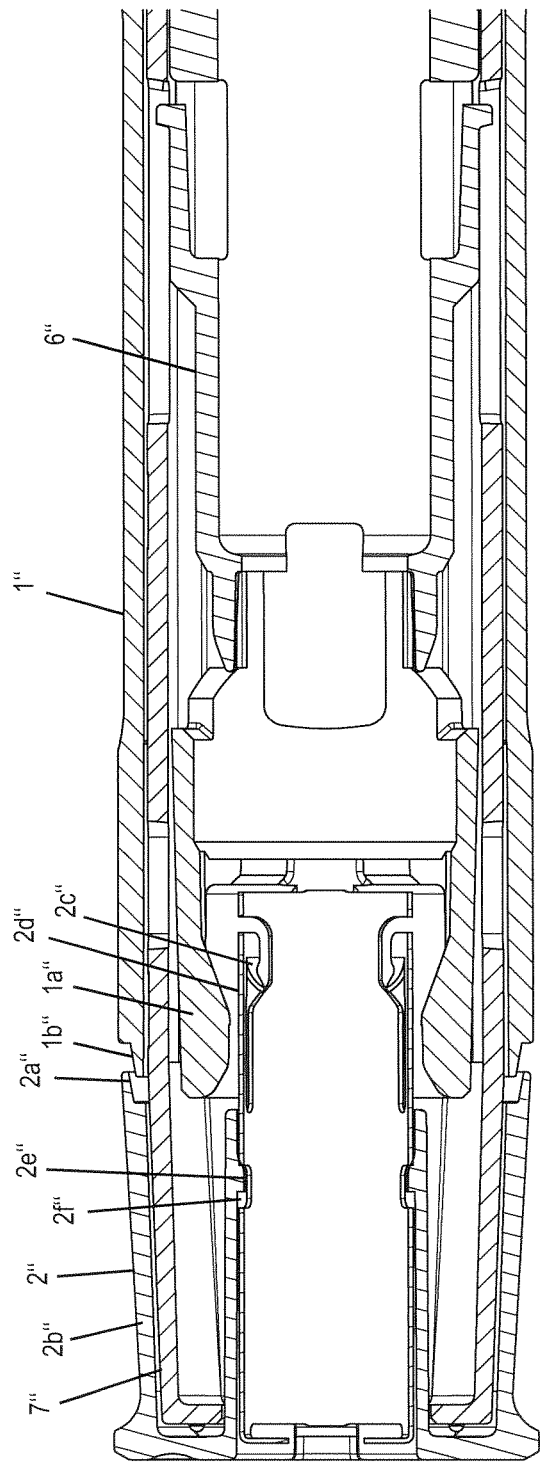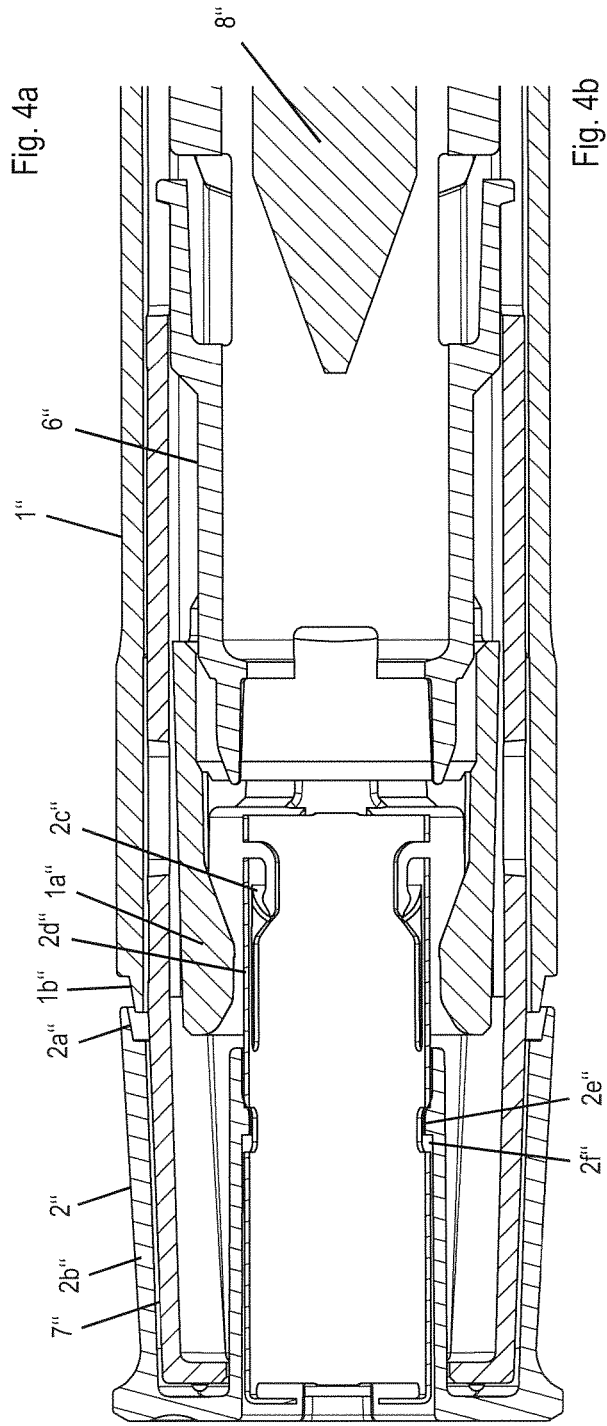

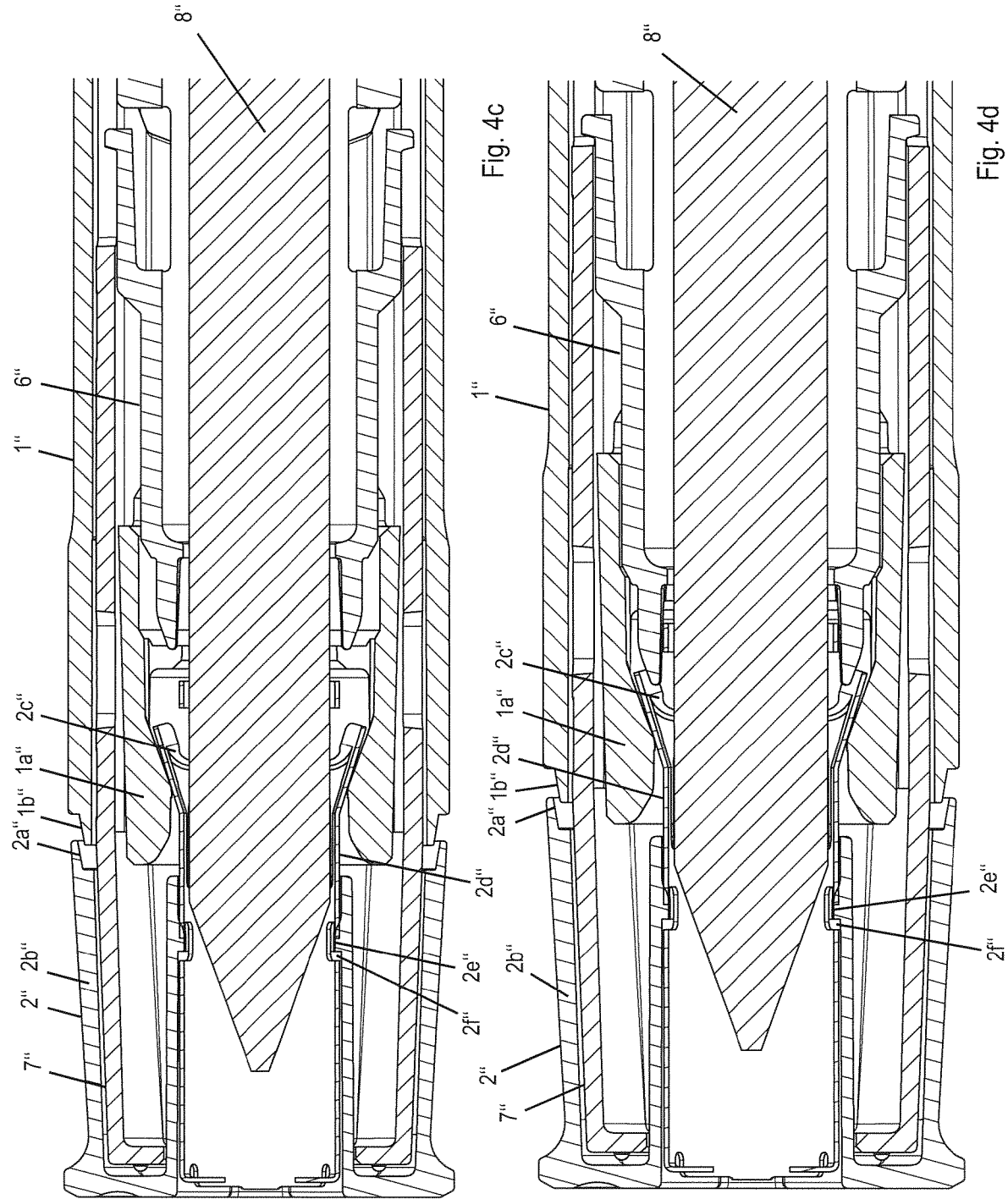

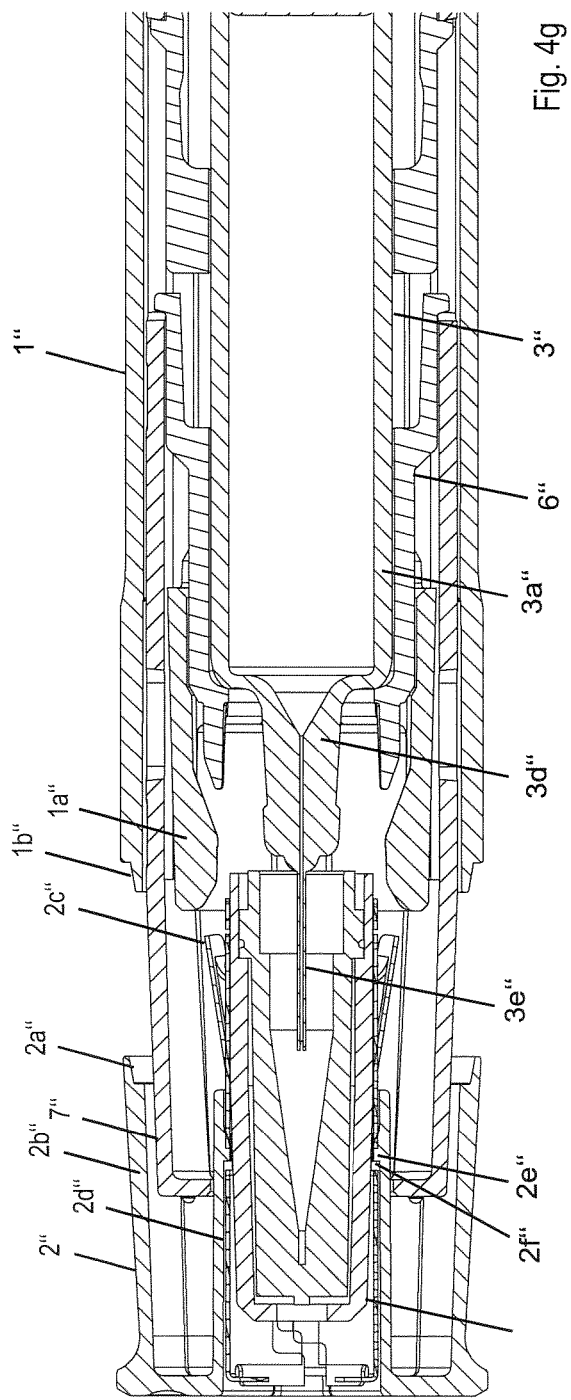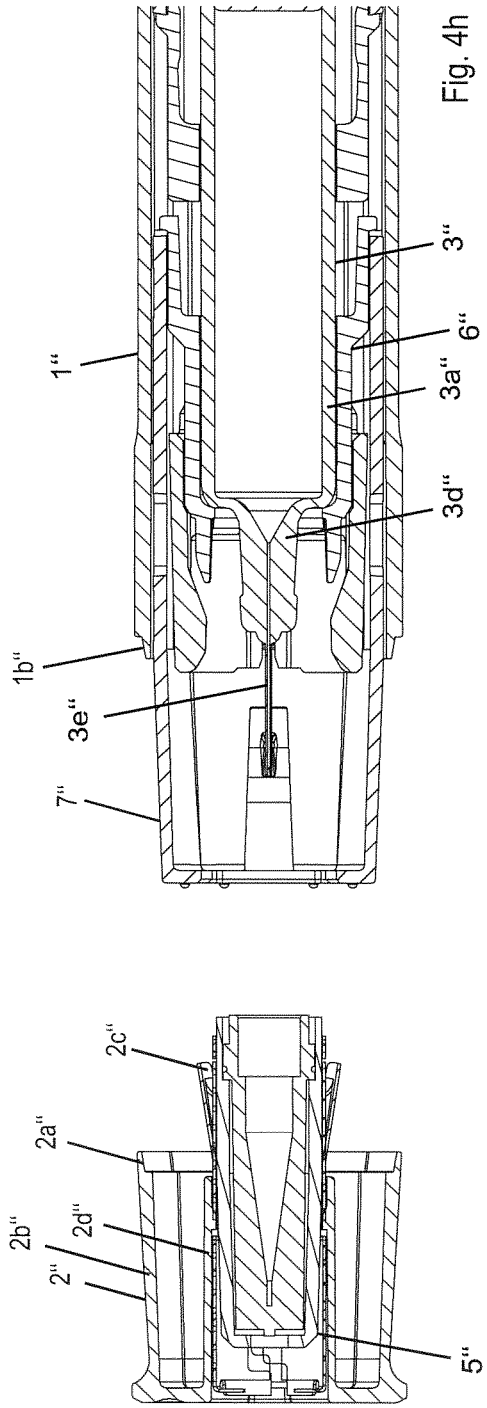

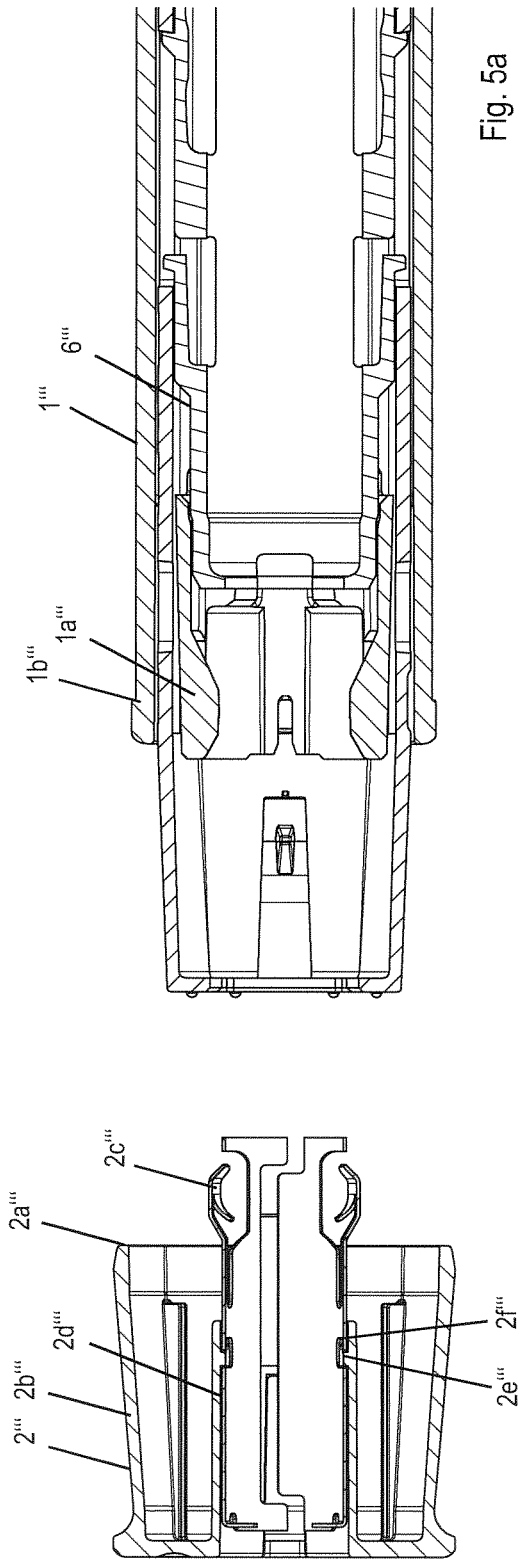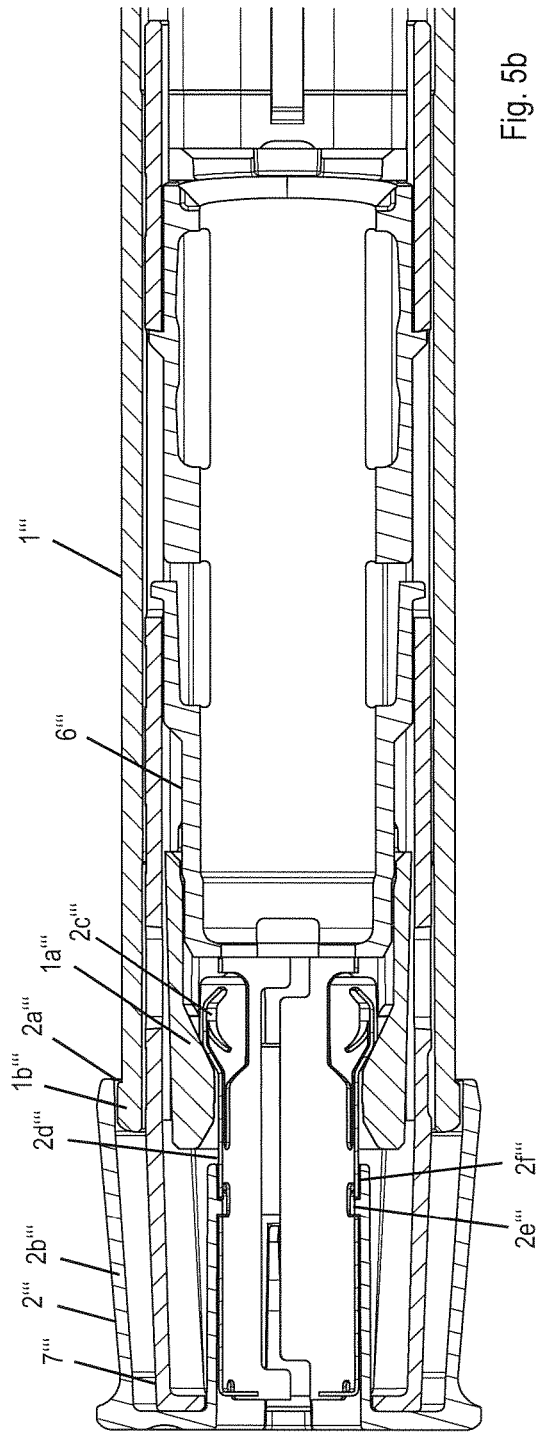

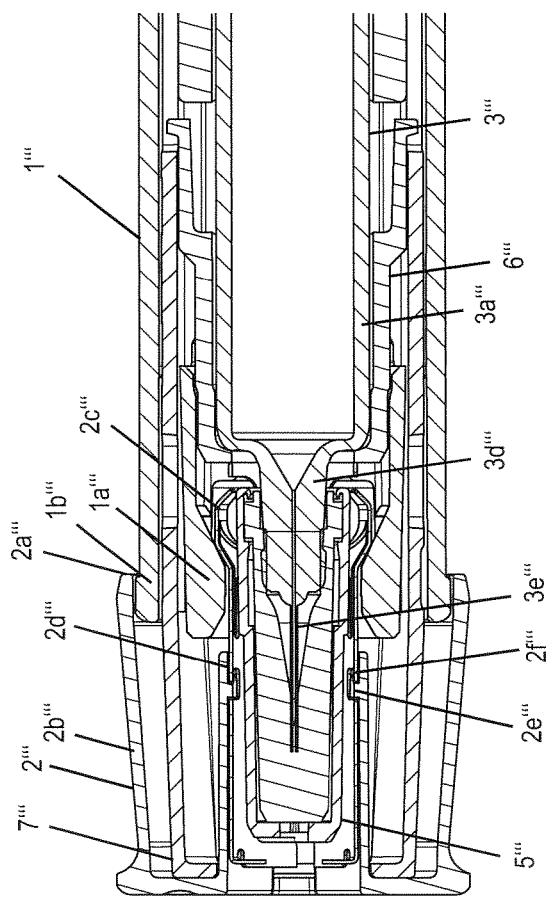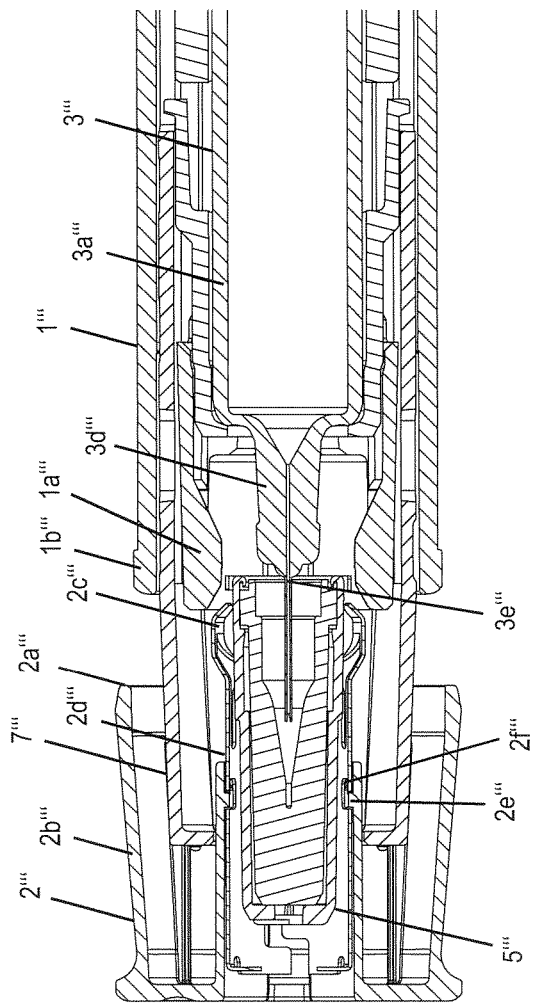

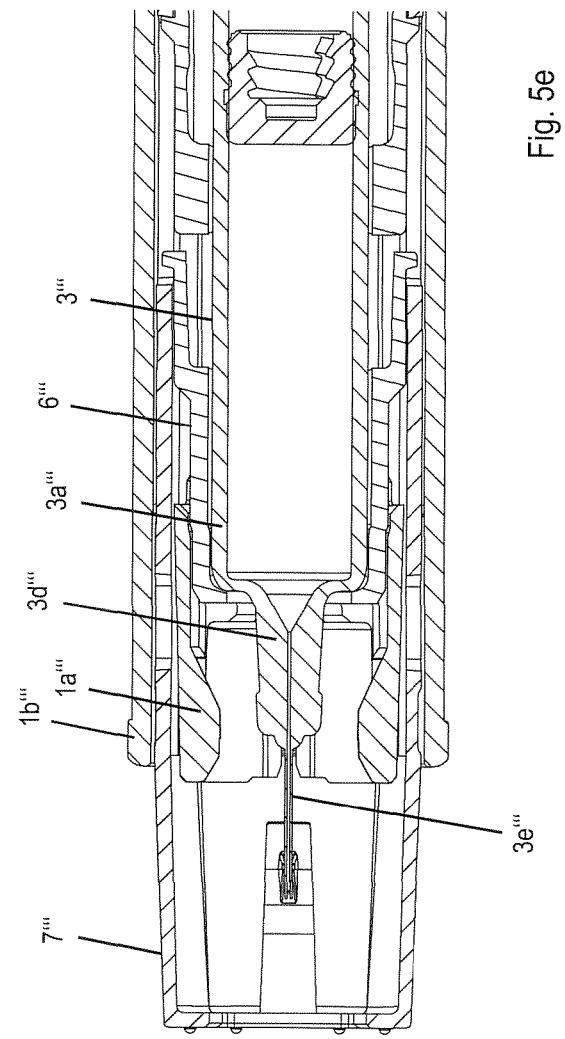
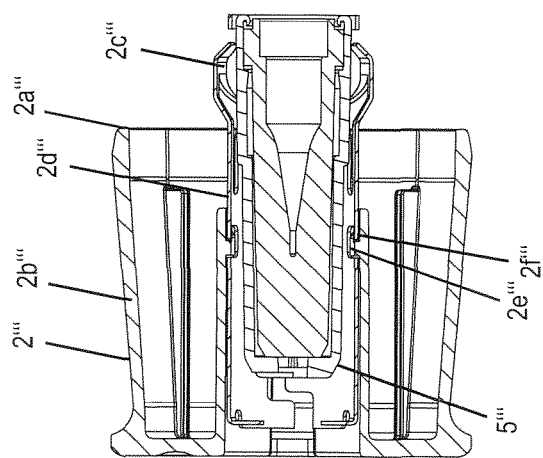
Fig. 5e

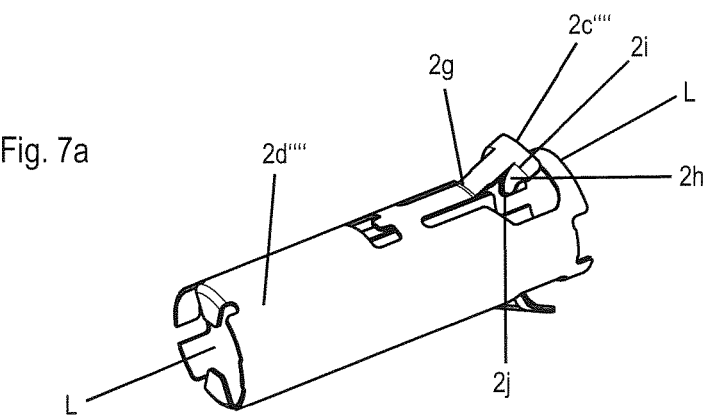
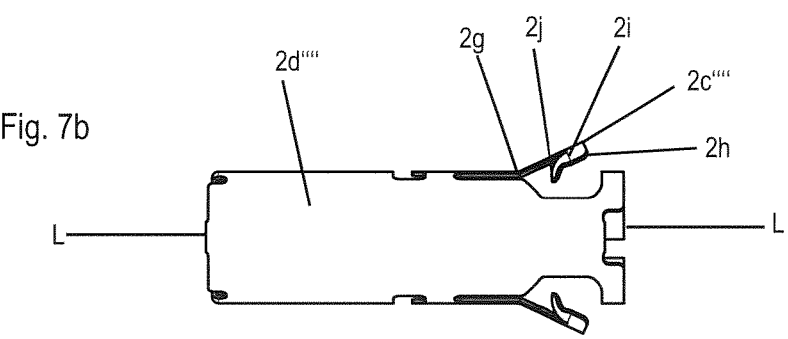
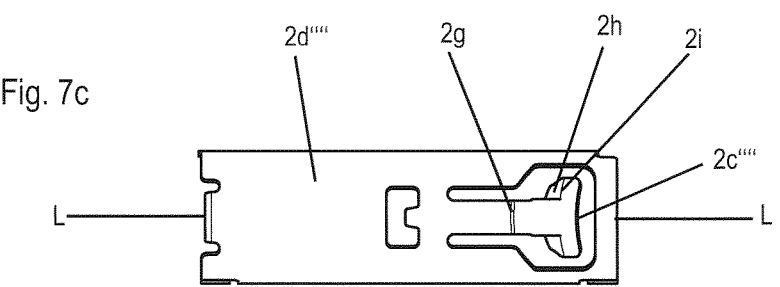

INJECTION DEVICE WITH OUTER CAP WITH NEEDLE PROTECTION CAP REMOVAL ELEMENT AND METHOD FOR ASSEMBLING AN INJECTION DEVICE

CROSS-REFERENCE TO RELATED APPLICATIONS

This application is a continuation of U.S. patent application Ser. No. 16/259,797 filed on Jan. 28, 2019, issued as U.S. Pat. No. 11,311,681 on Apr. 26, 2022, which in turn is a continuation of International Application No. PCT/CH2017/000074 filed Jul. 26, 2017, which claims priority to Swiss Application Nos. 00989/16 filed Jul. 28, 2016, and 01166/16, filed Sep. 8, 2016, respectfully, the entire contents of all of which are incorporated by reference herein in their entireties.

FIELD OF THE INVENTION

The invention relates to an injection device for administering a liquid product, more particularly a medicine. The invention further relates to a method for assembling and/or preparing an injection device for the administration of a fluid.

BACKGROUND

The term "medicine" in the present context comprises any flowable medical formulation that is suitable for controlled administration by a means such as a cannula or a hollow needle, the term comprising, for example, a liquid, a solution, a gel or a fine suspension that contains one or more medically active substances. A medicine can be a composition with a single active substance or a premixed or co-formulated composition with multiple active substances from a single container. Medicine comprises pharmaceuticals such as peptides (e.g. insulin, and insulin-containing medicines, preparations containing GLP-1 and derived or analogous substances), proteins and hormones, biologically obtained or active substances, active substances based on hormones or genes, nutritional formulations, enzymes and additional substances, both in solid (suspended) or liquid form, but also polysaccharides, vaccines, DNA or RNA or oligonucleotides, antibodies or parts of antibodies as well as suitable base, auxiliary and carrier substances.

SUMMARY OF THE INVENTION

Injection devices in which a prefilled syringe is arranged are known from the prior art. The prefilled syringe has an injection needle that is non-detachably connected to the prefilled syringe and via which the medicine contained in the prefilled syringe can be output. In order to keep the injection needle and the medicine in the prefilled syringe sterile, the injection needle is enclosed by a needle protection cap and sealed off in a sterile manner from the surroundings. Such needle protection caps can be designed as a soft needle shield (SNS) or a rigid needle shield (RNS). A soft needle shield (SNS) consists of an elastomeric part that surrounds the injection needle. A rigid needle shield (RNS) has multiple parts, in particular an elastomeric cap-like part and a hard, sleeve-like part made from a non-elastomeric plastic that surrounds the elastomeric part and is thus connected substantially non-detachably.

During the handling of the prefilled syringe, there is a danger that the sterility of the injection needle and the medicine can be endangered by force applied to the needle protection cap. This can occur particularly during the assembly process of the injection device, more particularly when the prefilled syringe is inserted in the syringe holder provided therefor into the injection device. The insertion of the prefilled syringe into the injection device is therefore a step that deserves special attention in consideration of the sterility of the injection needle and the medicine. It is known from WO 2010/136076 A1, U.S. Pat. No. 9,339,610 B2, WO 2015/144871 A1 and US 2016/0243315 A1 that the needle protection cap mounted on the prefilled syringe can also be pulled off, i.e. removed from the prefilled syringe during removal of a cap-like pull-off element, which is also referred to as a device cap, that is mounted at the distal end of the injection device and closes off the distal end of the injection device. The needle protection cap thus remains in the device cap. For this purpose, the device cap has engagement members that are brought into engagement with the needle protection cap when the device cap is being pulled off. When the pull-off movement of the pull-off element is continued, the engagement members entrain the needle protection cap, whereby it is removed from the prefilled syringe. In order to ensure secure removal of the needle-protection cap by removing the device cap, it is known from the prior art that the engagement members connected to the device cap come into engagement with the needle protection cap.

A solution provided by the invention is that of specifying an injection device and a method for assembly and/or preparation of an injection device for administering a product, which allows easy insertion of the product container into the injection device and/or secure removal of the needle-protection cap from the product container, without endangering the sterility of the injection needle and the medicine.

The solution is provided by the injection device according to claim 1 and the method according to independent claim 16. Advantageous improvements can be derived from the dependent claims, the description and the figures.

The invention proceeds from a device for administering a product, namely an injection device having a longitudinal axis (L). The injection device can be designed as a so-called autoinjector, which has a mechanism that effects automatic discharge of the product, e.g. by an energy accumulator, more particularly a spring, and optionally effects automatic insertion and/or retraction of the injection needle. In an autoinjector, the force for discharging the product is provided by an energy accumulator such as a spring. The injection device can alternatively be designed as a manual injection device, i.e. the force for discharging the product comes from muscular force, for example by the user. The injection device, whether it is an autoinjector or a manual injection device, can have a needle protection sleeve, which protrudes distally from the distal end of the injection needle after injection is finished, or is displaced into this position relative to the housing in order to prevent inadvertent access to the injection needle and thus reduce a risk of injury. In an autoinjector, the needle protection sleeve can also be used, for example, as a trigger element for triggering the product discharge, wherein the needle protection sleeve is displaced proximally in relation to the housing for this purpose. Alternatively, the autoinjector can be triggered by operating a trigger button of the autoinjector, wherein the needle protection sleeve is used as visual concealment before use of the autoinjector.

The injection device has a product container with an injection needle, e.g. a prefilled syringe or a syringe in general as known from the prior art. The product container can, for example, have a hollow cylindrical product container portion which supports a piston displaceably. The piston can form a sealing gap with the inner periphery of the product container portion and thus form a sterile barrier. The piston can be displaced in the distal direction, by means of a piston rod of the injection device for example, in order to discharge product from the product container via the injection needle. The injection needle can preferably be formed non-detachably on the product container. For example, the product container can have a holding portion, in particular a needle holding portion, which is arranged distally of the product container portion and is non-detachably connected to the injection needle and thus surrounds a proximal part of the injection needle, for example. The injection needle can thus protrude in the distal direction from the holding portion. The holding portion can have a smaller outer diameter than the product container portion, for example. The product container portion can taper at the distal end thereof toward the holding portion.

The term "distal" used herein relates to the direction in which the tip of the injection needle points. The term "proximal" used herein relates to the direction that is opposite to the distal direction. The distal end of the device is where the needle is located.

Furthermore, the concept "along the longitudinal axis (L)" includes both the concept "parallel to the longitudinal axis (L)" and the concept "approximately parallel to the longitudinal axis (L)."

A needle protection cap such as a soft needle shield (SNS) or a rigid needle shield (RNS) is mounted, more particularly detachably mounted, on the product container, for example the retaining portion. The needle protection cap can be fastened to the retaining portion by a friction fit or a form fit or by a combined friction-form fit. The needle protection cap encloses the injection needle and seals it off sterilely against the surroundings. A soft needle shield (SNS) comprises or consists of an elastomer such as a part formed on the basis of synthetic or natural rubber, which surrounds the needle. The soft needle shield (SNS) has a surface at the outer circumference that is formed from a soft material, e.g. a synthetic or natural rubber-like material. A rigid needle shield (RNS) has at least several parts, in particular an elastomeric cap-like inner part and a hard sleeve-like or cap-like outer part made from a non-elastomeric plastic that receives the elastomeric part and is thus connected substantially non-detachably. The outer sleeve-like or cap-like part surrounds the inner cap-like part and is connected non-detachably, for example to the inner cap, so that the inner and the outer caps form a unit. The outer part can be formed from a plastic harder than the inner part. The outer part can be made from polyethylene, polystyrene, polypropylene or some other suitable plastic, for example. The inner part can be formed from synthetic or natural rubber or some other suitable material.

At the distal end of the injection device or of a housing such as a receiving housing of the injection device, a device cap, which can also be referred to or designed as a closure cap or pull-off cap, can be secured and can close off the distal end of the housing or the receiving housing. The injection device can comprise a housing such as a receiving housing of the injection device for receiving the product container, wherein the product container has a fixedly connected injection needle and wherein the needle protection cap is detachably arranged on the product container. The needle protection cap encloses the injection needle and seals it off sterilely against the surroundings. The device cap can be connected to the housing or the receiving housing by a friction fit or a form fit such as a snap fit. During removal from the injection device and/or the housing, the device cap can be removable from the injection device, e.g. the housing or the receiving housing, by an axial movement or a combined axial/rotational movement.

The injection device can further comprise a product container holder, which is fixedly connected, in particular axially and rotationally fixedly connected, to the housing of the injection device. The product container holder can be used for receiving the product container, wherein the product container can be fixedly, in particular axially and rotationally fixedly, retained in the present container holder. Alternatively, the housing and the product container holder can be formed integrally. Alternatively, the product container holder can be arranged axially movably or rotatably relative to the housing.

The device cap, which is provided releasably at the distal end of the housing of the injection device, comprises one or more engagement elements in order to effect the removal of the needle protection cap from the product container when the device cap is removed from the injection device. The device cap, which is coupled to the engagement element, can be connected via the engagement element to the needle protection cap in such a manner that removing the device cap from the injection device effects the removal of the needle protection cap from the product container. In particular, at least a part of the movement or the entire movement of the device cap in the distal direction can be transmitted to the engagement element, i.e. the engagement element is entrained by the device cap so that the engagement element pulls the needle protection cap away from the product container, more particularly the retaining portion.

The engagement element can be deformed in such a manner that the engagement element can move from a spaced-apart position, in which the engagement element is at a radial distance from the needle protection cap, into an engagement position, in which the engagement element is engaged with the needle protection cap, wherein the engagement element is deformed during removal of the device cap. Furthermore, the engagement element is constructed such that during assembly of the injection device, more particularly when inserting the product container into the housing or into the product container holder, no force or a very small force, more particularly no or a very small force exerted by the engagement element, acts on the needle protection cap. This prevents the needle protection cap from being moved relative to the product container already during insertion of the product container. This reduces the risk that the sterility of the injection needle and the medicine can be compromised. This arrangement can also have the effect that no forces or very small forces exerted by the engagement element act on the needle protection cap during storage of the injection device.

In the delivery condition of the injection device, the engagement element can be in the spaced-apart position relative to the needle protection cap, for example. In the engagement position, the engagement element is arranged in relation to the needle protection cap such that a movement of the device cap in the distal direction effects an entrainment of the needle protection cap, and thus the needle protection cap is removed from the product container. In the engagement position of the engagement element, the engagement element engages at or in the needle protection cap. The engagement element can engage at or in an outer surface or at or in an edge or at or in a distal end face or at or in a proximal end face of the needle protection cap. The engagement element can especially preferably be formed with a hook shape. The hook-like engagement element can have a short limb and a long limb. Alternatively, the engagement element can have a different design in which the engagement element is at a distance from the needle protection cap radially in the spaced-apart position of the engagement element and is engaged with the needle protection cap in the engagement position of the engagement element, the engagement element being deformed during removal of the device cap.

In the spaced-apart position of the engagement element, the engagement element can be undeformed, deformed or deformed radially outwardly. In the engagement position of the engagement element, the engagement element can be undeformed, deformed or deformed radially inwardly. The engagement element can preferably be deformed plastically or elastically.

An irreversible deformation is referred to as a plastic deformation. The deformation of a material is plastic if the material does not reassume its original shape on its own. The material retains its shape after being subjected to a force or a load. A reversible deformation is referred to as an elastic deformation. The material can return to its initial condition after being subjected to a force or a load on the material.

The engagement element is made from metal, particularly steel, and particularly preferably stainless steel or spring steel. The engagement element is made from a material that has a bending strength that allows a plastic and/or elastic deformation. Especially preferably, the engagement element is designed such that it is plastically and/or elastically deformed in the spaced-apart position of the engagement element and plastically and/or elastically undeformed in the engagement position, or that it is plastically and/or elastically undeformed in the spaced-apart position of the engagement element and plastically and/or elastically deformed in the engagement position.

The engagement element can especially preferably be deformed radially outwardly plastically and/or elastically in the spaced-apart position of the engagement element, or alternatively, plastically and/or elastically undeformed. The engagement element can especially preferably be undeformed plastically and/or elastically in the engagement position of the engagement element, or alternatively deformed radially inwardly plastically and/or elastically. Especially preferably, the long limb of the hook-like engagement element can be deformed radially outwardly plastically and/or elastically in the spaced-apart position of the engagement element, or alternatively be undeformed plastically and/or elastically and the short limb of the hook-like engagement element can protrude radially inwardly. In the engagement position of the engagement element, the long limb of the hook-like engagement element can especially preferably be undeformed plastically and/or elastically, or alternatively be deformed plastically and/or elastically, more particularly deformed radially inwardly, and the short limb of the hook-like engagement element can protrude radially inwardly, wherein the short limb of the engagement element is engaged, more particularly always engaged, with the outer surface of the needle protection cap. The outer surface of the needle protection cap can have one or more openings or one or more fastening means with which the engagement element can engage or into which it can bore in the engagement position. Alternatively, the needle protection cap does not have an opening or a fastening means, in which case the engagement element in the engagement position can engage with or bore into the outer surface of the needle protection cap.

The hook-like engagement element can have a long and a short limb, the long and the short limbs being connected to one another. The engagement element can be formed from a stamped-bent part. The stamped-bent part is plastically and/or elastically deformable. The stamped-bent part is preferably made from metal, particularly steel, and particularly preferably stainless steel or spring steel. The stamped-bent part is made from a material that has a bending strength that preferably allows a plastic and/or elastic deformation. The long limb of the engagement element can be deformable at an angle transverse to the longitudinal axis (L). The long limb of the engagement element can be deformed radially inwardly or radially outwardly at an angle transverse to the longitudinal axis (L), more particularly at an angle of less than 90° transverse to the longitudinal axis (L). The long limb extends along the longitudinal axis (L), wherein the long limb can be deformable radially inwardly or radially outwardly, more particularly plastically and/or elastically deformable. The short limb of the engagement element protrudes radially inwardly. The short limb of the engagement element is preferably tooth-shaped or triangular or has an acute angle. The sides of the tooth-shaped or triangular or acute-angled short limb can be straight or curved. The short limb preferably has two curved sides and one straight side. A tip of the tooth-shaped or triangular or acute-angled short limb of the engagement element can preferably protrude radially inwardly. The tip of the tooth-shaped or triangular or acute angle short limb is preferably arranged opposite the straight side of the tooth-shaped or triangular or acute-angled short limb. The tip of the short limb can be claw-like in shape. The tip of the short limb of the engagement element can be engaged with the needle protection cap in the engagement position in which the engagement element is engaged with the needle protection cap, more particularly always engaged with the needle protection cap. The short limb of the engagement element is designed such that the short limb can come into engagement with the needle protection cap or can be engaged with the needle protection cap.

In one embodiment, the long limb extends along the longitudinal axis (L), and the long and the short limbs of the engagement element can be connected to one another, in particular connected with a plastic or elastic deformation, such that the short limb extends from the long limb radially inwardly at an angle, more particularly at an angle of less than 90°, transverse to the longitudinal axis (L). Especially preferably, the long and the short limbs of the engagement element can be connected to one another in such a manner that the straight side of the tooth-shaped or triangular or acute-angled short limb extends radially inwardly at an angle, more particularly an angle of 90°, transverse to the longitudinal axis (L), and the tip of the short limb of the engagement element protrudes radially inwardly. During removal of the device cap, in which the engagement element is in the engaged position, the tensile force acts transversely to the straight side of the tooth-shaped or triangular or acute-angled short limb of the engagement element, the straight side of the tooth-shaped or triangular or acute-angled short limb being connected to the long limb at an angle, more particularly at an angle of 90° transverse to the longitudinal axis (L). The thickness of the tooth-shaped or triangular or acute-angled short limb, in particular the thickness of the stamped-bent part or of the metal for the tooth-shaped or triangular or acute-angled short limb can be or become adapted such that the device cap for the injection device can always be securely removed.

In an alternative embodiment, the long limb extends along the longitudinal axis (L), and the long limb and the short limb of the engagement element can be connected to one another, more particularly connected with a plastic or elastic deformation, such that the short limb extends radially inwardly from the long limb at an angle, more particularly radially inwardly at an angle relative to the longitudinal axis (L), along the longitudinal axis (L). Especially preferably, the long and the short limbs of the engagement element can be connected to one another in such a manner that the straight side of the tooth-shaped or triangular or acute-angled short limb is connected to the long limb along the longitudinal axis (L), and the tip of the short limb of the engagement element protrudes radially inwardly. During removal of the device cap, wherein the engagement element is in the engaged position, the tensile force acts along the straight side of the tooth-shaped or triangular or acute-angled short limb of the engagement element, and the straight side of the tooth-shaped or triangular or acute-angled short limb is connected to the long limb along the longitudinal axis (L). The length of the straight side of the tooth-shaped or triangular or acute-angled short limb, more particularly the length of the straight side of the tooth-shaped or triangular or acute-angled short limb that is connected to the long limb, can be or become adapted in such a manner that the device cap can be securely pulled off the injection device.

In addition, multiple short limbs can be provided on the long limb. The multiple short limbs can be arranged in a circumferential direction around the longitudinal axis (L) transversely to the longitudinal axis (L) and/or along the longitudinal axis (L). The multiple short limbs can be designed in different manners. The short limbs are preferably tooth-shaped, triangular or acute-angled in shape. The distance between the straight side and the tip of the tooth-shaped or triangular or acute-angled short limb can be different. The multiple short limbs produce a secure engaging or a secure engagement with the needle protection cap, with which the needle protection cap can be pulled off the injection device. Due to the different distances between the straight side and the tip of the tooth-shaped or triangular or acute-angled limb, the limbs can engage offset relative to the longitudinal axis (L) with the needle protection cap, and the needle protection cap can be securely pulled off the injection device.

The long limb of the engagement element can be deformed, in particular plastically and/or elastically, in particular the long limb of the engagement element can be deformed at an angle of less than 90° transverse to the longitudinal axis (L) in such a manner that the short limb of the engagement element can move from a spaced-apart position, in which the short limb of the engagement element is a radial distance from the needle protection cap, into an engaged position, in which the short limb of the engagement element is engaged with the needle protection cap, while the long limb of the engagement element deforms, in particular plastically or elastically, during removal of the device cap. The long limb of the engagement element can be deformed plastically or elastically during removal of the device cap.

Alternatively or additionally, the engagement element, more particularly the short limb of the engagement element, can have a fastening element that can enter in the engaged position of the engagement element into a fixed, more particularly axially and radially fixed, connection with the needle protection cap. The fastening element of the engagement element can form a fixed connection with the outer surface or an edge of the needle protection cap. One or more openings or one or more fastening means can be provided on the outer surface or on the edge of the needle protection cap, and the fastening element of the engagement element can enter into a fixed connection with the opening or the fastening means of the needle protection cap. Alternatively, the needle protection cap does not have an opening or a fastening means, in which case the fastening element of the engagement element can engage with or bore into the outer surface or the edge of the needle protection cap.

The device cap can additionally have a sleeve, wherein the sleeve can partially comprise the engagement element. The sleeve can preferably have an inner sleeve and an outer sleeve. The engagement element can be connected axially movably to the inner sleeve or preferably axially fixedly. The engagement element can preferably be connected axially movably to the inner sleeve, or preferably axially fixedly, to the inner sleeve. The sleeve can preferably be formed from plastic. Alternatively, the sleeve can be formed from metal. The sleeve can be connected to the housing of the injection device by a friction fit or a form fit such as a snap fit. For this purpose, an engagement member can be provided on the outer sleeve and can be detachably engaged with a mating engagement member arranged on the housing. During removal of the device cap from the injection device and/or the housing, the sleeve can be removable from the injection device, e.g. the housing, by an axial movement or a combined axial/rotational movement.

The device cap can additionally have a sleeve-like or cylindrical remover element, wherein the engagement element can be provided on the remover element. Especially preferably, the long limb of the engagement element can be connected to the remover element. The remover element can be sleeve-like or cylindrical in shape, wherein the engagement element, more particularly the long limb of the engagement element, can be attached to a proximal end of the remover element. Alternatively, the engagement element can be provided in and/or on an outer surface of the remover element, in particular in and/or on an outer surface of the sleeve-like or cylindrical remover element. The long limb of the engagement element can be mounted in and/or on the outer surface of the sleeve-like or cylindrical remover element. The remover element and the engagement element are preferably connected axially fixedly and non-rotationally to one another. The remover element and the engagement element can be constructed in one or two parts. The remover element and the engagement element can preferably be formed from the same material. It is especially preferred that the remover element and the engagement element are formed from a stamped-bent part. The stamped-bent part is plastically and/or elastically deformable. The stamped-bent part is preferably made from metal, particularly steel, and particularly preferably stainless steel or spring steel. The stamped-bent part is formed from a material that has a bending strength that allows a plastic and/or elastic deformation. The stamped-bent part can be bent into a sleeve shape or a cylindrical shape. The remover element and the engagement element can alternatively be formed from different materials. The sleeve can surround the remover element, which has a sleeve-like or cylindrical shape for example, preferably clasping it over the periphery thereof. The remover element is preferably an element separate from the sleeve but which is connected to the sleeve, e.g. displaceably or non-displaceably along the longitudinal axis (L). The remover element can preferably have one or more protrusions that are latched into recesses formed on the sleeve in order to form an axially fixed connection between the sleeve and the remover element. The remover element can preferably be connected displaceably or non-displaceably to the inner sleeve of the sleeve, wherein the recesses are provided on the inner sleeve.

Furthermore, one or more blocking elements can be provided on the housing or on a part fixedly connected to the housing, wherein the blocking element or elements, in the engagement position, keep the engagement element engaged with the needle protection cap or bring it into engagement. The blocking element can comprise a first and/or second oblique surface, more particularly a first and/or second inwardly protruding oblique surface. The first and the second oblique surfaces of the blocking element can have an inclination. The first and the second oblique surfaces can be inclined relative to one another. The engagement element of the device cap is coupled to the blocking element of the housing in such a manner that, during removal of the device cap from the injection device, the engagement element is movable or is moved relative to the needle protection cap and, during this movement, more particularly an axial movement or a combined axial-rotational movement, can be deformed or is deformed by means of the blocking element of the housing in such a manner that the engagement element, more particularly the short limb of the engagement element, is or becomes engaged with the needle protection cap. In the engagement position of the engagement element, the engagement element is axially fixedly connected to the needle protection cap, the needle protection cap being entrained by the engagement element of the device cap during the continuation of the axial movement, or the combined axial/rotational movement, of the device cap. In other words, the stroke in the distal direction along the longitudinal axis (L) relative to the housing that is carried out by the device cap during removal from the injection device comprises a first partial stroke, during which the device cap is movable or is moved relative to the needle protection cap, and a second partial stroke, during which the needle protection cap follows the movement of the device cap or is entrained by the device cap.

The invention also relates to a method for assembling an injection device and/or for preparing an injection device for the administration of a product. The injection device can be the injection device described herein, for example.

The method comprises the step of providing a housing or a receiving housing, which can be part of a housing of the injection device, for example, for receiving a product container. The housing or the receiving housing can be elongated or have a sleeve-like shape.

The method further comprises the step of providing a device cap, which can be removably attached to the distal end of the housing. The method further comprises the step of attaching the device cap to the distal end of the housing. The device cap can be snap-fit to the housing, for example. The device cap comprises one or more engagement elements in order to effect the removal of the needle protection cap from the product container when the device cap is removed from the injection device. The engagement element can be designed in a hook shape. The hook-like engagement element can have a long and a short limb, the long and the short limbs being connected to one another.

The device cap can further comprise a remover element, wherein the engagement element can be arranged on the remover element. Especially preferably, the long limb of the engagement element can be connected to the remover element. The remover element and the engagement element can be constructed in one or two parts. The device cap can further comprise a sleeve, wherein the sleeve can surround the sleeve-like or cylindrical remover element, preferably clasping it via the periphery thereof. The remover element is preferably an element separate from the sleeve but which is connected to the sleeve, e.g. displaceably or preferably non-displaceably along the longitudinal axis (L). The engagement element and the remover element are preferably formed from a different material than the sleeve. The sleeve is preferably formed from plastic. The engagement element and the remover element are preferably formed from the same material.

The method further comprises providing the product container, which has a fixedly connected injection needle, a needle protection cap that is detachably arranged on the production container and that encloses the injection needle and seals it off sterilely from the surroundings. The product container can be a prefilled syringe, as known from the prior art, for example, or a syringe in general. The product container can comprise a hollow cylindrical product container portion, for example, with a piston being displaceably arranged in the product container. The piston is used, for example, to discharge, by means of a piston rod of the injection device, product from the product container via the injection needle. The injection needle can preferably be formed non-detachably on the product container. The product container can additionally comprise a holding portion, more particularly a needle-holding portion, which is arranged distally of the product container portion and is non-detachably connected to the injection needle. The needle-holding portion of the product container can surround a proximal part of the injection needle. The injection needle can thus protrude in the distal direction from the holding portion. The holding portion can have a smaller outer diameter than the product container portion. The product container portion can taper at the distal end thereof toward the holding portion. The needle protection cap, which surrounds the injection needle and preferably seals it off against the surroundings sterilely, is arranged on the product container, more particularly on the holding portion of the product container.

The method further comprises pushing or inserting the product container with the detachably connected needle protection cap into the housing along a longitudinal axis (L) in a distal direction, wherein the engagement element, in particular the long limb of the engagement element, is deformable or is deformed or pre-deformed in such a manner that the needle protection cap is at a radial distance from the engagement element during pushing or insertion of the product container relative to the housing in the distal direction. This has the effect that no or very small forces are exerted on the needle protection cap during insertion of the product container. This prevents the needle protection cap from being moved relative to the product container already during insertion of the product container. This reduces the risk that the sterility of the injection needle and the medicine can be compromised.

The engagement element, in particular the long limb of the engagement element, is preferably deformable in such a manner that, during removal of the device cap from the injection device, the engagement element can be brought into engagement with the needle protection cap.

In the spaced-apart position of the engagement element, the engagement element, in particular the long limb of the engagement element, can be undeformed, deformed or deformed radially outwardly. In the engagement position of the engagement element, the engagement element, in particular the long limb of the engagement element, can be undeformed, deformed or deformed radially inwardly. The engagement element, in particular the long limb of the engagement element, is plastically or elastically deformable. The engagement element, in particular the long limb of the engagement element, is preferably made from metal, particularly steel, particularly preferably stainless steel or spring steel. The engagement element, in particular the long limb of the engagement element, is formed from a material that has a bending strength that allows a plastic and/or elastic deformation.

Alternatively, the engagement element can have a design that differs from a hook shape, wherein the engagement element is at a radial distance from the needle protection cap in the spaced-apart position of the engagement element and is engaged with the needle protection cap in the engagement position of the engagement element, the engagement element being deformed during removal of the device cap.

Especially preferably, the engagement element, in particular the long limb of the engagement element, is designed such that it is plastically and/or elastically deformed in the spaced-apart position of the engagement element and plastically and/or elastically undeformed in the engagement position, or in particular that it is plastically and/or elastically undeformed in the spaced-apart position of the engagement element and plastically and/or elastically deformed in the engagement position.

The engagement element can especially preferably be deformed radially outwardly plastically and/or elastically in the spaced-apart position of the engagement element, or alternatively, plastically and/or elastically undeformed. The engagement element can especially preferably be undeformed plastically and/or elastically in the engagement position of the engagement element, or alternatively deformed radially inwardly plastically and/or elastically. Especially preferably, the long limb of the hook-like engagement element can be deformed radially outwardly plastically and/or elastically in the spaced-apart position of the engagement element, or alternatively be undeformed plastically and/or elastically and the short limb of the hook-like engagement element can protrude radially inwardly. In the engagement position of the engagement element, the long limb of the hook-like engagement element can especially preferably be undeformed plastically and/or elastically, or alternatively deformed plastically and/or elastically, more particularly deformed radially inwardly, and the short limb of the hook-like engagement element can protrude radially inwardly, wherein the short limb of the engagement element is engaged, more particularly always engaged, with an outer surface of the needle protection cap.

Before pushing or insertion of the product container in the distal direction relative to the housing, in particular before pushing or insertion of the product container into the housing of the injection device, the engagement element is deformed, preferably deformed radially outwardly.

For example, the long limb of the hook-shaped engagement element can be deformed, preferably deformed radially outwardly, more particularly deformed radially outwardly plastically and/or elastically, while the short limb protrudes radially inwardly. The long limb of the engagement element can be deformed at an angle, in particular an angle of less than 90° transversely to the longitudinal axis (L), in particular deformed plastically and/or elastically, in particular deformed radially outwardly plastically or elastically. The short limb protrudes radially inwardly. An assembly tool can be used for this deformation, in order to bring the engagement element into a spaced-apart position in which the engagement element is at a radial distance from the needle protection cap. The assembly tool can be designed as an assembly mandrel or as a spreading mandrel. In the process, the engagement element can be plastically and/or elastically deformed, the engagement element being formed from a plastic and/or elastic material.

A stamped-bent part can be used to form the hook-shaped engagement element. The stamped-bent part is plastically and/or elastically deformable. At least one long limb and at least one short limb of the engagement element are stamped from a metal, preferably steel, particularly preferably stainless steel, more particularly stainless steel or spring steel. The long limb and the short limb of the engagement element are connected to one another. The long limb extends along the longitudinal axis (L). In one embodiment, the connection between the long and the short limb of the engagement element is deformed, more particularly plastically or elastically deformed, such that the short limb extends from the long limb radially inwardly at an angle, more particularly at an angle of less than 90°, transversely to the longitudinal axis (L). In an alternative embodiment, the connection between the long and the short limbs is deformed, more particularly plastically deformed, such that the short limb extends radially inwardly from the long limb at an angle, more particularly an angle relative to the longitudinal axis (L), along the longitudinal axis (L).

Furthermore, at least one long limb can be stamped from the metal and several short limbs can be provided on the long limb in order to form the engagement element.

The long limb can additionally be deformed at an angle of less than 90° transverse to the longitudinal axis (L), more particularly plastically and/or elastically deformed, such that the engagement element moves into a spaced-apart position and/or into an engagement position. The long limb can be deformed radially inwardly or outwardly at an angle, in particular an angle of less than 90° transverse to the longitudinal axis (L), in particular deformed plastically and/or elastically.

The stamped-bent part can comprise the engagement element and the remover element. The engagement element and the remover element can be stamped from the stamped-bent part, and after the stamping, the remover element, more particularly the remover element and/or the engagement element, can be formed into a sleeve shape or cylindrical shape.

The engagement element, particularly the long limb of the engagement element of the device cap can be deformed prior to the releasable attachment of the device cap to the housing of the injection device, preferably deformed radially outwardly, in particular deformed radially outwardly plastically and/or elastically. Alternatively, the engagement element, particularly the long limb of the engagement element of the device cap, can be deformed, preferably deformed radially outwardly, more particularly deformed plastically and/or elastically radially outwardly, after the device cap has been releasably attached to the housing of the injection device. Alternatively, the engagement element, in particular the long limb of the engagement element, can be deformed during attachment of the device cap to the housing, preferably deformed radially inwardly, more particularly deformed radially inwardly plastically and/or elastically.

The engagement element, based on the material thereof, in particular the bending strength of the material, can remain plastically and/or elastically deformed or alternatively can be kept in the plastic and/or elastic shape by means of a part of the injection device, in particular a part of the housing and/or a product container, wherein the product container can be received in the product container holder.

One or more blocking elements, which hold the engagement element in engagement with the needle protection cap or bring it into engagement, are preferably provided on the housing or on a part fixedly connected to the housing, or on the product container holder. The blocking element comprises a first and/or second oblique surface, more particularly a first and/or second inwardly protruding oblique surface. The first and the second oblique surfaces of the blocking element can have an inclination. The first and the second oblique surfaces can be inclined relative to one another. When the engagement element is engaged with the needle protection cap, the engagement element is in the engagement position. In the engagement position of the engagement element, the engagement element can form a fixed connection to the needle protection cap, more particularly an axially and radially fixed connection. The engagement element preferably connects to an outer surface of the needle protection cap, wherein the engagement element engages with or bores into the outer surface of the needle protection cap. In the engagement position of the engagement element, the engagement element engages at or in the needle protection cap. The engagement element, more particularly the short limb of the engagement element, can engage at or in an outer surface or at or in an edge or at or in a distal end face or at or in a proximal end face of the needle protection cap. The outer surface of the needle protection cap can additionally comprise one or more openings or one or more fastening means, wherein the engagement element can engage with or bore into these openings or fastening means in the engagement position. Alternatively, the needle protection cap does not have an opening or a fastening means, in which case the engagement element, more particularly the short limb of the engagement element, can engage with or bore into the outer surface of the needle protection cap.

The engagement element, more particularly the short limb of the engagement element, can further comprise a fastening element. The fastening element can be connected to the needle protection cap in the engagement position of the engagement element fixedly, more particularly axially and/or radially fixedly. The fastening element of the engagement element can form a fixed connection to the outer surface or to an edge of the needle protection cap. One or more openings or one or more fastening means can be provided on the outer surface or on the edge of the needle protection cap, wherein the fastening element of the engagement element can fixedly connect itself to the opening or the fastening means of the needle protection cap. Alternatively, the needle protection cap does not have an opening or a fastening means, in which case the fastening element of the engagement element can engage with or bore into the outer surface or the edge of the needle protection cap.

The blocking element can be used to move the engagement element into the engagement position when the device is being pulled off. The engagement element, in particular the long limb of the hook-shaped engagement element, can slide along the first oblique face of the blocking element and deform in the process, in particular plastically and/or elastically. During an axial movement or a combined axial-rotational movement of the device cap relative to the housing of the injection device, the device cap initially moves in the distal direction relative to the needle protection cap. During a continuation of the pull-off movement of the device cap, the engagement element comes into engagement with the needle protection cap, wherein the blocking element, more particularly the first oblique face of the blocking element, has the effect that the engagement element is brought into the undeformed shape, is deformed or is deformed radially inwardly. For example, the long limb of the hook-shaped engagement element can be brought in this case into the undeformed shape, can be deformed or can be deformed radially inwardly, while the short limb of the hook-shaped engagement element protrudes radially inwardly and is engaged with the needle protection cap, more particularly always engaged with the needle protection cap. After the engagement element is in the engagement position and the device cap is pulled further, the device cap entrains the needle protection cap. The injection device is available for an injection.

Alternatively, the blocking element can be used to deform the engagement element of the device cap plastically and/or elastically during assembly of the injection device. During placement of the device cap on the housing of the injection device, the blocking element of the housing, in particular the second oblique face of the blocking element, can have the effect that the engagement element of the device cap is deformed, more particularly deformed radially inwardly. For example, the long limb of the hook-shaped engagement element can be deformed, more particularly deformed radially inwardly, while the short limb protrudes radially inwardly. In the process, the engagement element of the device cap slides over the oblique second face of the blocking element of the housing. At the end of the placement movement of the device cap, the engagement element can deform or bring itself or be brought into the undeformed shape or can become deformed radially outward. The engagement element of the device cap moves transversely to the longitudinal axis (L), the engagement element being positioned offset proximally to the blocking element of the housing. When the device cap has been placed on or attached to the housing of the injection device, the engagement element of the device cap is preferably undeformed. For example, the long limb of the hook-shaped engagement element is designed to be undeformed, while the short limb protrudes radially inwardly.

A needle protection sleeve, which is used to protrude past the distal end of the injection needle before or after a finished injection, can preferably also be inserted at least partially into the housing, the device cap being placed at a distal end of the needle protection sleeve. The device cap can be connected to the needle protection sleeve by a friction fit or a form fit such as a snap fit.

The reader is further referred to the features that are disclosed in conjunction with the device described herein, which also advantageously improve the device for the method.

BRIEF DESCRIPTION OF THE DRAWINGS

The invention has been described with reference to multiple embodiments and examples. Especially preferred embodiments of the invention will be described below with reference to the figures. The features disclosed therein advantageously improve the invention individually and in any combination of features. In the drawings:

FIG. 1 shows a longitudinal sectional view of a first embodiment of an injection device according to the invention, wherein a device cap (2) is releasably arranged on the injection device.

FIGS. 2a-2g show longitudinal sectional views of the distal part of the injection devices from FIG. 1, wherein the individual assembly steps for assembling the device cap (2) on the injection device according to FIG. 1 can be seen.

FIGS. 2h and 2i show longitudinal sectional views of the distal part of the first embodiment of the injection device, wherein the removal of the device cap (2) from the injection device can be seen.

FIGS. 3a-3d show longitudinal section views of a distal part of a second embodiment of an injection device according to the invention, wherein the individual assembly steps for assembling the device cap (2') on this injection device can be seen.

FIGS. 4a-4f show longitudinal sectional views of a distal part of a third embodiment of an injection device according to the invention, wherein the individual assembly steps for assembling a device cap (2") on this injection device can be seen.

FIGS. 4g and 4h show longitudinal sectional views of the distal part of the third embodiment of the injection device, wherein the removal of the device cap (2") from the injection device can be seen.

FIGS. 5a-5c show longitudinal sectional views of a distal part of a fourth embodiment of an injection device according to the invention, wherein the individual assembly steps for assembling the device cap (2''') on this injection device can be seen.

FIGS. 5d and 5e show longitudinal sectional views of the distal part of the fourth embodiment of the injection device, wherein the removal of the device cap (2''') from the injection device can be seen.

FIG. 6b shows a perspective view along the longitudinal axis (L) of the first embodiment of the engagement element (2c'''') according to FIG. 6a.

FIG. 7a shows a perspective view of the first embodiment of the engagement element (2c'''') with the longitudinal axis (L), wherein a remover element (2d'''') and the engagement element (2c'''') can be seen, and the engagement element (2c'''') is deformed, more particularly deformed elastically and plastically radially outwardly.

FIG. 7b shows a perspective view along the longitudinal axis (L) of the first embodiment of the engagement element (2c'''') according to FIG. 7a.

FIG. 7c shows a perspective view of the first embodiment of the engagement element (2c'''') according to FIG. 7b, wherein the view is rotated by 90° relative to the view of FIG. 7b.

FIG. 8b shows a perspective view along the longitudinal axis (L) of the second embodiment of the engagement element (2c''''') according to FIG. 8a.

FIG. 9b shows a perspective view along the longitudinal axis (L) of the second embodiment of the engagement element (2c''''') according to FIG. 9a.

DETAILED DESCRIPTION

Figure 2B:
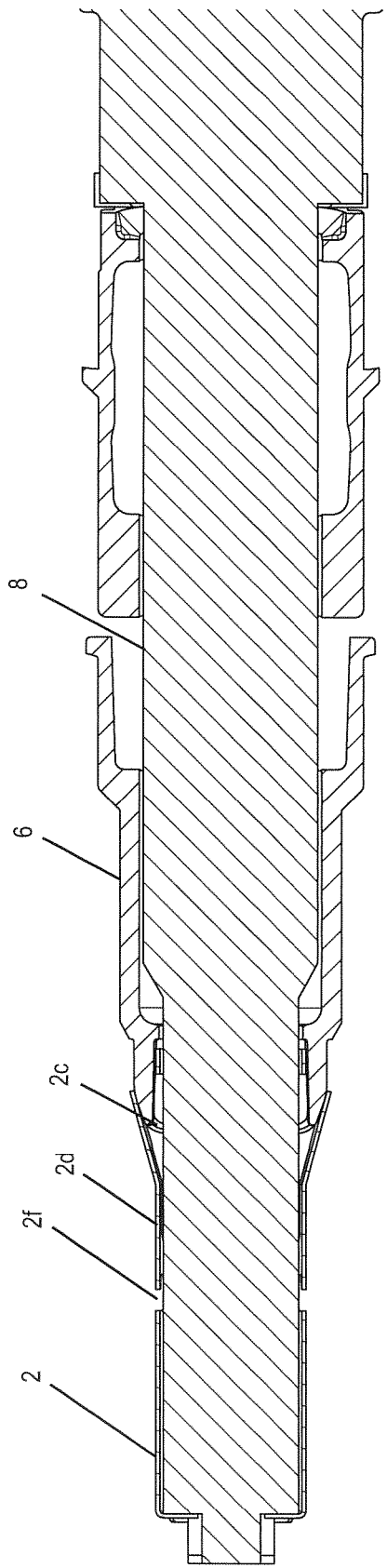
Figure 2C:
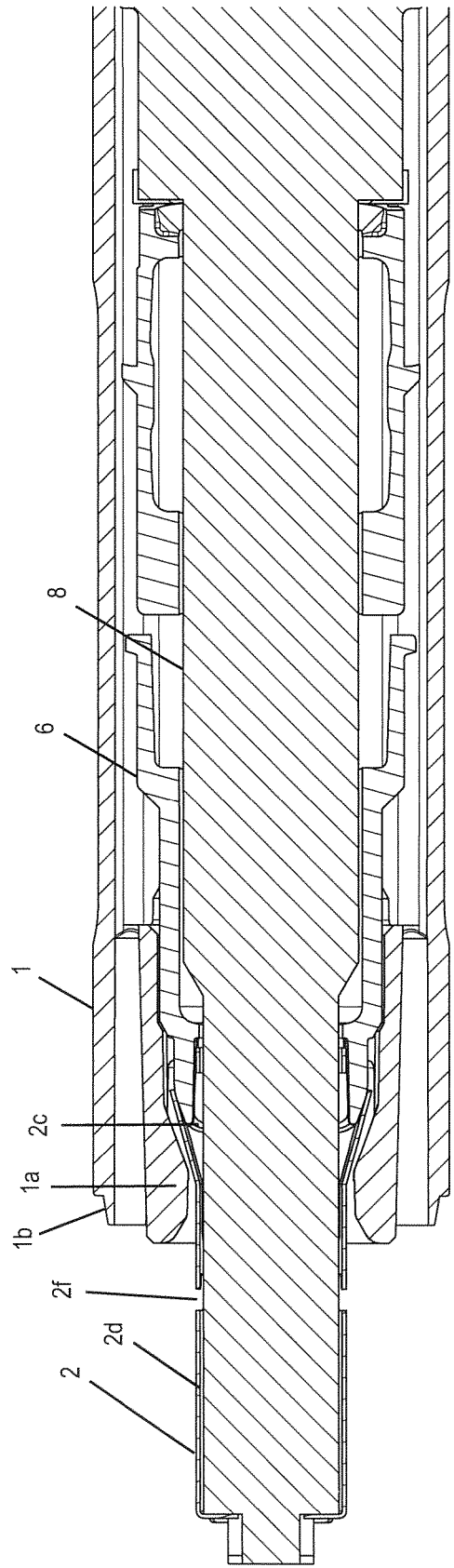
Figure 2D:
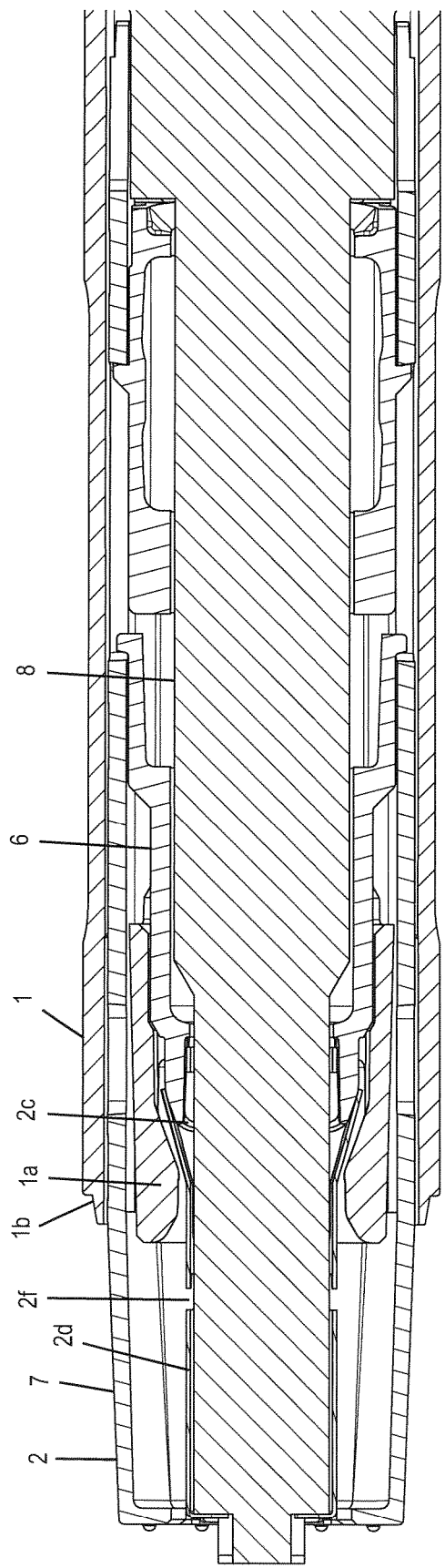
Figure 2E:
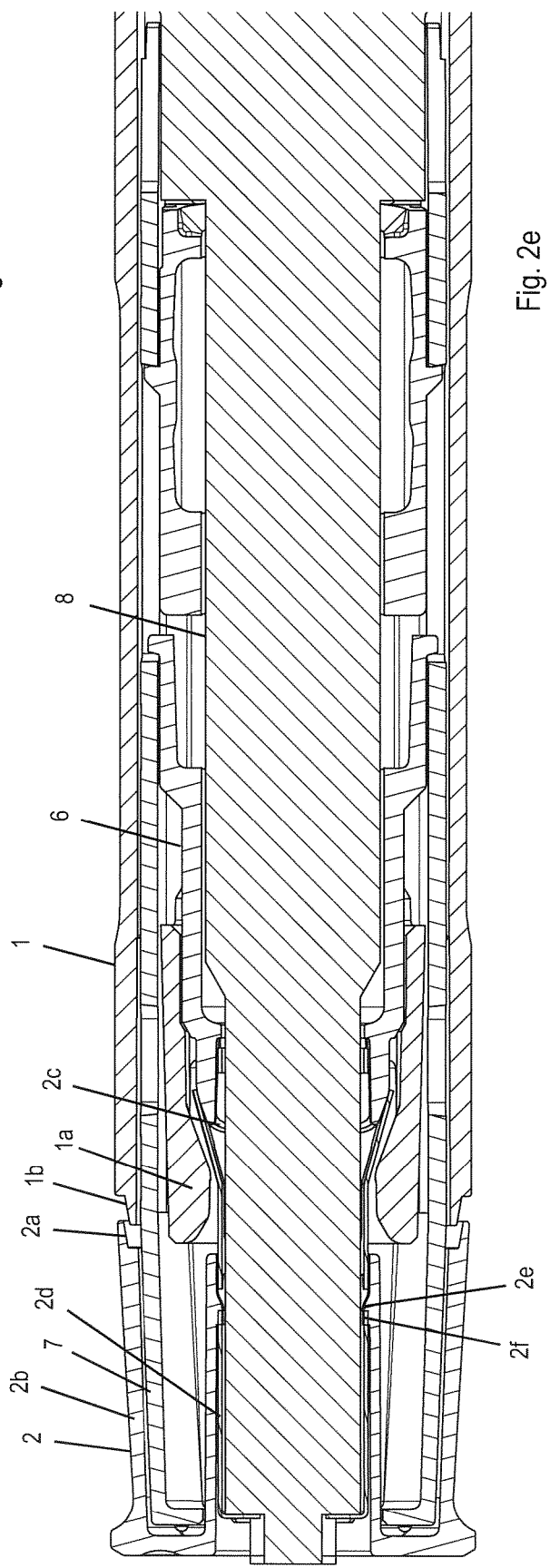

FIG. 1 shows a longitudinal sectional view of a first embodiment of an injection device according to the invention, wherein a device cap (2) is releasably arranged on the injection device. The injection device can have the device cap (2) placed on the distal end in a delivery state, for example. The injection device comprises a housing (1). The housing (1) can be formed as a sleeve-like, more particularly a cylindrical receiving housing (1) having a distal and a proximal part. The device cap (2) is releasably provided at the distal end of the housing (1). The device cap (2) is releasably fastened to the distal end of the housing (1) or, alternatively, the distal end of the needle protection sleeve (7), via a form-fitting connection, in particular a snap connection. The device cap (2) further comprises a sleeve (2b). The sleeve (2b) can preferably have an inner sleeve and an outer sleeve. The sleeve (2b) can preferably be formed from plastic. In order to establish the form-fitting connection between the device cap (2) and the housing (1), the device cap (2) can have one or more engagement members (2a) that can engage, in particular be snap-fit, with mating engagement members (1b) correspondingly arranged on the housing (1) of the injection device. The sleeve (2b) extends, like the housing (1), along the longitudinal axis (L) of the injection device. By a movement of the device cap (2) about and/or along the longitudinal axis (L), the form-fitting connection, in particular the snap-fit connection, between the device cap (2) and the housing (1) of the injection device or, alternatively, the needle protection sleeve (7), can be released, and the device cap (2) can be removed in the distal direction from the housing (1) of the injection device. The distal end of the sleeve (2b) is substantially closed off, so that access to the interior of the device cap (2) from the outside is not possible or is only possible with great difficulty.

The device cap (2) comprises an engagement element (2c). The engagement element (2c) is plastically and/or elastically deformable. The engagement element (2c) is preferably made from metal, particularly steel, and particularly preferably stainless steel or stainless spring steel. The engagement element (2c) is formed from a material that has a bending strength that allows a plastic and/or elastic deformation. The engagement element (2c) can be deformed in such a manner that it becomes deformed, more particularly deformed radially outwardly or radially inwardly, or assumes an undeformed shape. The engagement element (2c) can be deformed in such a manner that it becomes deformed, more particularly deformed radially outwardly or radially inwardly, or is or becomes undeformed. The engagement element (2c) is hook-shaped, wherein the engagement element (2c) has a long and a short limb.

The device cap (2) can further comprise a remover element (2d). The remover element (2d) is preferably sleeve-shaped, and the engagement element (2c) can be provided on the remover element (2d). The remover element (2d) and the engagement element (2c) are preferably formed from the same material. The remover element (2d) and the engagement element (2c) are preferably formed from a stamped-bent part. The stamped-bent part is plastically and/or elastically deformable. The stamped-bent part is preferably made from metal, particularly steel, especially preferably stainless steel, more particularly stainless spring steel. The stamped-bent part is formed from a material that has a bending strength that allows a plastic and/or elastic deformation.

The sleeve (2b) can surround, at least in part, the engagement element (2c), more particularly the remover element (2d) together with the engagement element (2c). The sleeve (2b) and the remover element (2d) with the engagement element (2c) are axially fixedly connected to one another. The sleeve (2b) and the remover element (2d) with the engagement element (2c) are constructed in two parts. The remover element (2d) is axially fixedly connected to the sleeve (2b), more particularly snap-fit, glued, overmolded or interlocked. For that purpose, the sleeve (2b), more particularly the inner sleeve of the sleeve (2b), can have a protrusion (2e) that is latched into a recess (2f) provided on the remover element (2d).

A product container (3) configured as a syringe is arranged in the housing (1) of the injection device. The product container (3) has a product container portion (3a), which is in particular hollow cylindrical in shape and the inner wall of which forms a sealing gap with a piston (3b) movably arranged in the product container portion (3a), in order to thereby form a sterile barrier. A flange (3c), also referred to as a finger flange, can be arranged at the proximal end of the product container portion (3a). The product container portion (3a) tapers at the distal end thereof to a needle holding portion (3d), which has a markedly smaller outside diameter than the product container portion (3a). The needle holding portion (3d) surrounds the proximal part of the injection needle (3e) and is thus preferably non-detachably connected. The product container (3) has a permanently connected injection needle (3e). The injection needle (3e) protrudes from the needle holding portion (3d) in the distal direction. By displacing the piston (3b) in the distal direction, the product arranged between the injection needle (3d) and the piston (3b) in the product container portion (3a), preferably a liquid product, can be output through the injection needle (3e).

In order to move the piston (3b) of the product container (3) in the distal direction, a drive unit can be provided in the housing (1) of the injection device. Alternatively, the drive unit can be frictionally and/or form fittingly connected and/or integrally bonded to the housing (1) of the injection device. The drive unit can comprise a piston rod (4). By displacing the piston rod (4) in the distal direction, a product can be discharged from the product container (3).

A needle protection cap (5) is detachably mounted on the needle holding portion (3d), e.g. form fittingly or frictionally connected. The needle protection cap (5) can be a rigid needle shield (RNS) or a soft needle shield (SNS). The needle protection cap (5) encloses the injection needle (3e) and seals the injection needle (3e) off sterilely against the surroundings. The needle protection cap (5) surrounds the injection needle (3e) such that the sterility thereof in relation to the surroundings is guaranteed.

The engagement element (2c) of the device cap (2) can be deformed in such a manner that the engagement element (2c) can move from a spaced-apart position, in which the engagement element (2c) is at a radial distance from the needle protection cap (5), into an engagement position of the engagement element (2c), in which the engagement element (2c) is engaged with the needle protection cap (5), wherein the engagement element (2c) is deformed during removal of the device cap.

This has the effect that, during insertion of the product container (3) into the housing (1) of the injection device, no or very small forces act on the needle protection cap (5), and in particular no or very small forces are exerted by the engagement element (2c).

A blocking element (1a) is provided on the housing (1) of the injection device or on a part fixed relative to the housing (1). The blocking element (1a) has at least one first oblique face. The first oblique face of the blocking element (1a) protrudes inwardly. The first oblique face of the blocking element (1a) has an inclination. Alternatively, the blocking element (1a) can be provided on the product container holder (6). When the device cap (2) is pulled off the housing (1), the engagement element (2c) of the device cap (2) can interact with the blocking element (1a) of the housing (1), in particular with the first oblique face of the blocking element (1a), in such a manner that the engagement element (2c) of the device cap (2) moves into the engagement position, in which the engagement element (2c) of the device cap (2) comes into engagement with the needle protection cap (5). The blocking element (1a) of the housing (1) keeps or brings the engagement element (2c) of the device cap (2) in or into the engagement position of the engagement element (2c).

The product container (3) can optionally be arranged in a product container holder (6), sleeve-like in shape for example. The tapering portion of the product container portion (3a) can be supported in the distal direction on an inward-projecting shoulder of the product container holder (6), for example. Alternatively, the flange (3c) of the product container (3) can be supported in the distal direction on the product container holder (6). Further alternatively, the product container holder (6) can frictionally retain the product container (3) at the product container portion (3a) thereof. The product container holder (6) can be arranged axially fixedly or movably in the housing (1) of the injection device, for example.

In the housing (1) of the injection device, a needle protection sleeve (7) can optionally be arranged and can be shifted in the proximal direction in relation to the housing (1) of the injection device in order to initiate product discharge and, after product discharge has concluded, can be shifted in the distal direction in order to cover the tip of the needle (3e) to reduce the risk of injury. Additionally or alternatively, the device cap (2) can be releasably connected to the needle protection sleeve (7), e.g. by a snap connection. Such needle protection sleeves (7) are known from the prior art and can be considered an advantageous improvement of the invention.

The injection device according to the invention can have any shape, provided that the injection device comprises a product container (3) in a housing (1). The injection device can be equipped as an autoinjector known from the prior art, in which a product is automatically discharged. But other injection devices can also be provided.

Longitudinal sectional views of the distal part of the injection devices from FIG. 1 can be seen in FIGS. 2a-2g, wherein the individual assembly steps for assembling the device cap (2) on the injection device according to FIG. 1 can be seen. Furthermore, longitudinal sectional views of the distal part of the of the injection device from FIG. 1 can be seen in FIGS. 2h and 2i, wherein the removal of the device cap (2) from the injection device can be seen. A sleeve-like product container holder (6) is placed on an assembly tool (8), more particularly an assembly mandrel tool (8). The product container holder (6) is displaced from the distal end of the assembly tool (8) relative to the assembly tool (8). The product container holder (6) is displaced in the proximal direction on the assembly tool (8) until the product container holder (6) assumes a proximal position. The product container holder (6) is used for receiving the product container (3). The sleeve-like remover element (2d) of the device cap (2), which comprises an engagement element (2c), is then placed on the assembly tool (8). The engagement element (2c) of the device cap (2) is deformed radially outwardly, in particular elastically and/or plastically outwardly. The long limb of the hook-shaped engagement element (2c) is deformed plastically and/or elastically radially outwardly, while the short limb of the hook-shaped engagement element (2c) protrudes radially inwardly. The radially outwardly deformed engagement element (2c) slides during displacement relative to the assembly tool (8) in the proximal direction over the distal end of the product container holder (6), wherein the remover element (2d) assumes a distal position. The outwardly deformed engagement element (2c), more particularly the elastically and/or plastically radially outwardly deformed long limb and/or the short limb of the engagement element (2c), is supported on the distal end of the product container holder (6). This support is used so that a premature engagement between the engagement element (2c) and the needle protection cap (5) does not occur. Thereafter, the housing (1) is placed on the assembly tool (8). The housing (1) is pushed in the proximal direction relative to the assembly tool (8) until the blocking element (1a) provided on the housing (1), more particularly the first oblique face of the blocking element (1a), comes into the region of the radially outwardly deformed engagement element (2c), more particularly into the region of the radially outwardly deformed long limb of the hook shaped engagement element (2c), but preferably does not contact it. The radially outwardly deformed engagement element (2c) and the first oblique face of the blocking element (1a) are arranged approximately parallel to one another. Alternatively, the product container holder (6) and the housing (1) can be formed integrally, in which case the step of positioning the product container holder (6) can be omitted. Additionally, a needle protection sleeve (7) can be placed on the assembly tool (8), wherein the needle protection sleeve (7) is displaced by the distal end of the assembly tool (8) relative to the assembly tool (8). The needle protection sleeve (7) is inserted at least in part into the housing (1) of the injection device. It is alternatively possible that the injection device does not comprise a needle protection sleeve (7), in which case this step can be omitted. Thereafter, the sleeve (2b) of the device cap (2) can be put onto the assembly tool (8). The sleeve (2b) of the device cap (2) is attached at the distal end of the housing (1). The sleeve (2b) is in particular releasably connected via a snap connection to the housing (1) or, alternatively, to the needle protection sleeve (7). The sleeve (2b), more particularly the outer sleeve of the sleeve (2b), comprises one or more engagement members (2a), which can engage with correspondingly provided matching engagement members (1b) provided on the housing (1). The protrusion (2e) provided on the sleeve (2b), more particularly on the inner sleeve of the sleeve (2b), latches into the recess (2f) provided on the remover element (2d). The sleeve (2b) is axially fixedly connected to the remover element (2d). The sleeve (2b), more particularly the outer sleeve of the sleeve (2b), partially surrounds the needle protection sleeve (7). The sleeve (2b) is placed at the distal end of the needle protection sleeve (7). Thereafter, the assembly tool (8) is removed. The subassembly consisting of at least the housing (1) and the device cap (2), wherein the device cap (2) comprises the engagement element (2c), can optionally be delivered for further assembly to a different assembly area. To produce the injection device, the product container (3) can be inserted into the product container holder (6) or into the housing (1) of the injection device. No or very little force is applied by the engagement element (2c) of the device cap (2) to the product container cap (5), which is releasably arranged on the product container (2). The injection needle (3e) of the product container (3) is sealed off sterilely against the surroundings by the needle protection cap (5). The product container (3), prefilled with the product, is inserted into the housing (1) from a proximal end of the housing (1). The product container (3) is pushed in the distal direction relative to the product container holder (6) or to the housing (1) until it reaches a distal end position. The engagement element (2c) of the device cap (2) is in the spaced-apart position, in which the engagement element (2c) is at a radial distance from the needle protection cap (5), which is arranged on the product container (3). Thereafter, a drive unit can be placed in the housing (1) of the injection device. The drive unit can be inserted from the proximal end of the housing (1) into the housing (1). Alternatively, the drive unit can be frictionally and/or form fittingly connected and/or integrally bonded to the housing (1) of the injection device. This completes the assembly of the injection device. The injection device is in the delivery condition. To use the injection device, the device cap (2) is removed from the distal end of the housing (1) of the injection device. This releases the form-fitting connection between the sleeve (2b), more particularly the outer sleeve of the sleeve (2b) of the device cap (2), more particularly the engagement member (2a) of the sleeve (2b), and the housing (1), more particularly the mating engagement member (1b) of the housing (1). Due to the axially fixed connection between the sleeve (2b) and the remover element (2d), wherein the remover element (2d) is axially fixedly connected to the engagement element (2c), the sleeve (2b) moves in the distal direction relative to the housing (1). In this movement, the engagement element (2c), more particularly the long limb of the hook-shaped engagement element (2c) of the device cap (2), slides over the first oblique face of the blocking element (1a) of the injection device housing (1). The engagement element (2c) is deformed in such a manner that the engagement element (2c) comes into engagement with the needle protection cap (5). The engagement element (2c) of the device cap (2) moves into the engagement position, in which the engagement element (2c) engages with the needle protection cap (5), wherein the engagement element (2c) is deformed during removal of the device cap (2), more particularly plastically and/or elastically deformed. The engagement element (2c), more particularly the long limb of the hook-shaped engagement element (2c), preferably reaches an undeformed shape or a shape deformed radially inwardly, and the engagement element (2c), more particularly the short limb of the hook-shaped engagement element (2c), forms an axially fixed connection to the needle protection cap (5). The engagement element (2c), more particularly the short limb of the hook-shaped engagement element (2c), engages with or bores into an outer surface of the needle protection cap (5). During the continuation of the removal movement, the needle protection cap (5) is entrained by the device cap (2), the needle protection cap (5) being removed from the product container (3) and held in the device cap (2). The needle protection cap (5) is received by the device cap (2). The injection device can be used for administering the product.

Figure 3C:
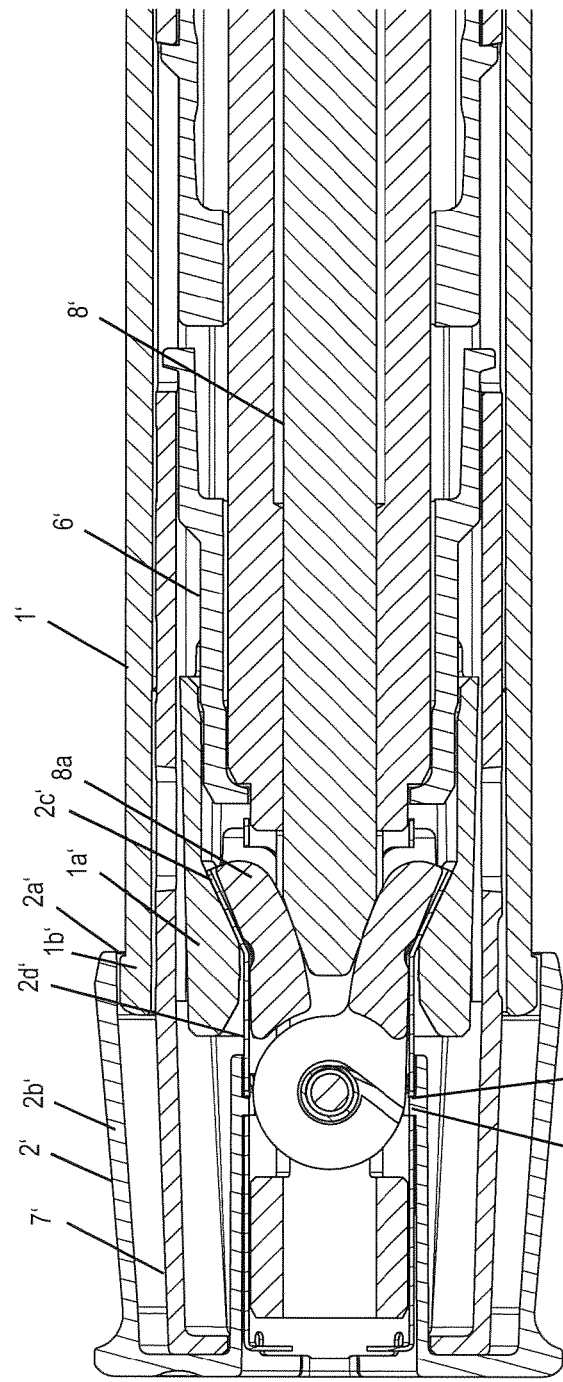
Figure 3D:
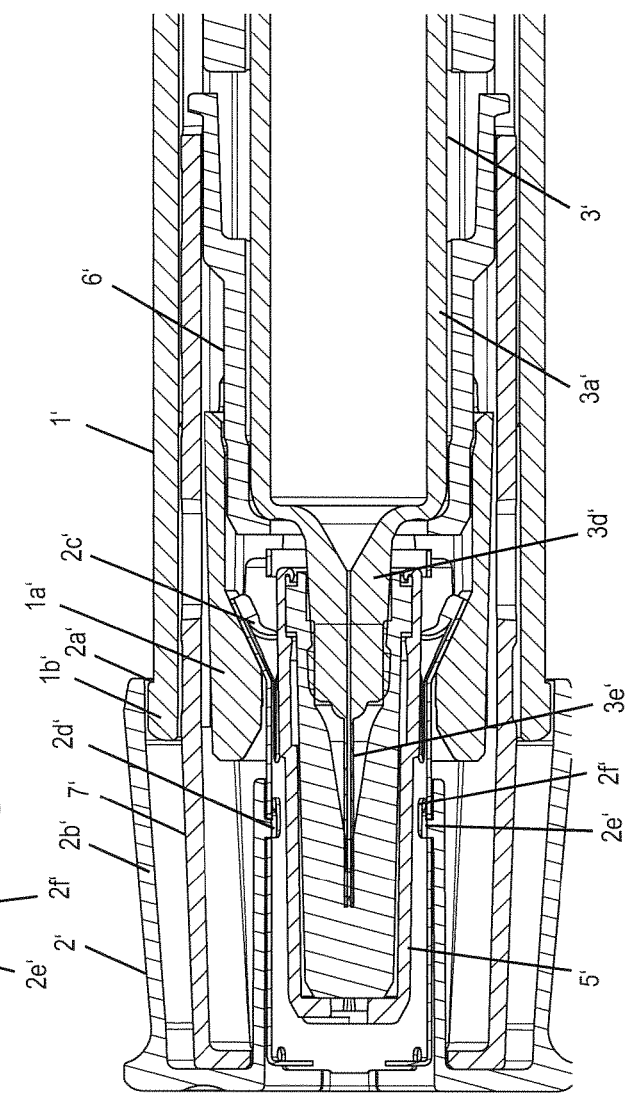
Figure 3E:
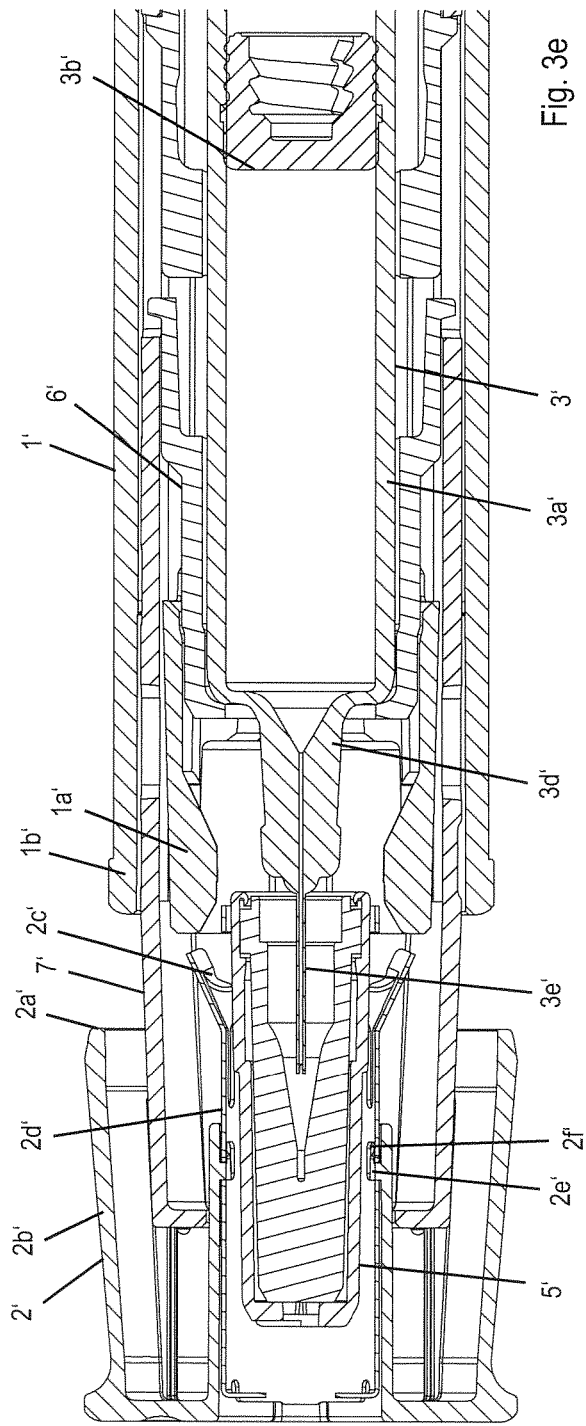
FIGS. 3e and 3f show longitudinal sectional views of the distal part of the second embodiment of the injection device, wherein the removal of the device cap (2') from the injection device can be seen.
Figure 3F:
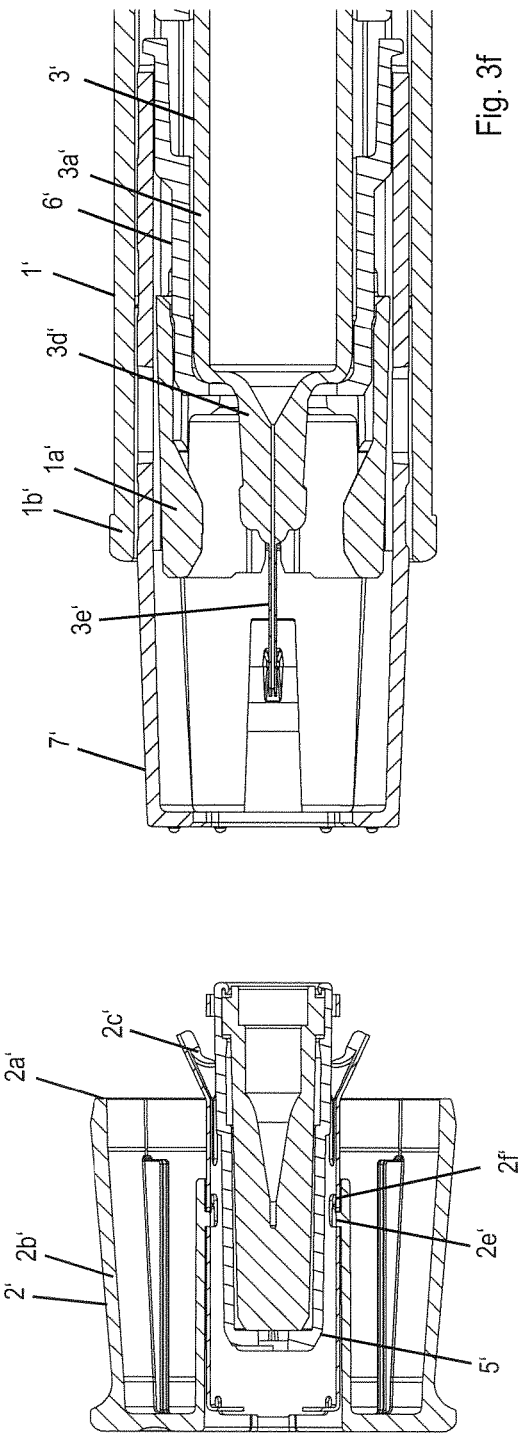
Figure 4E:
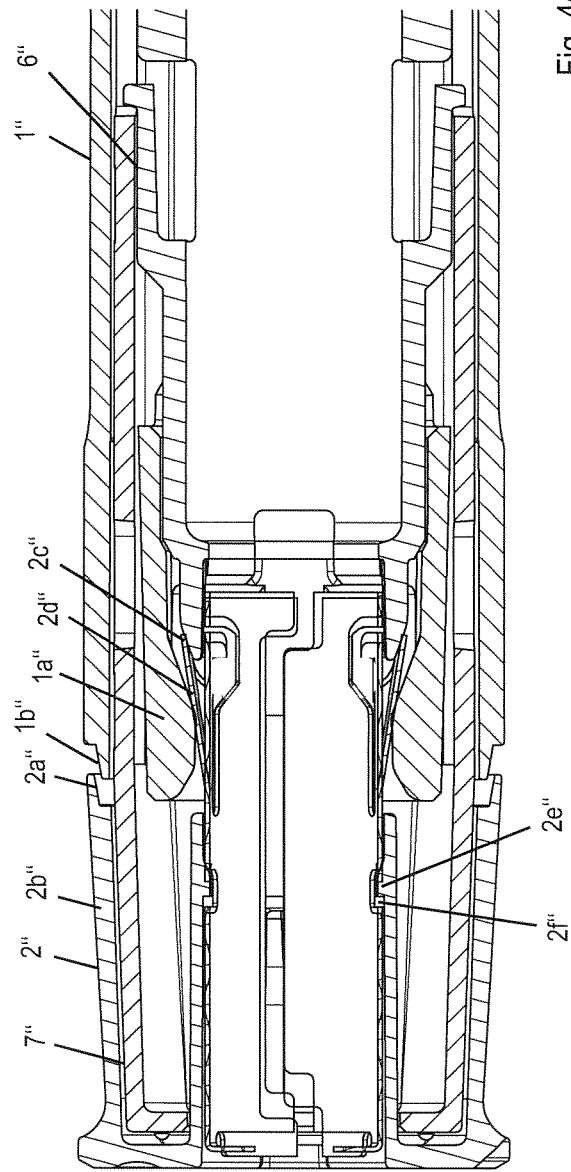
Figure 4F:
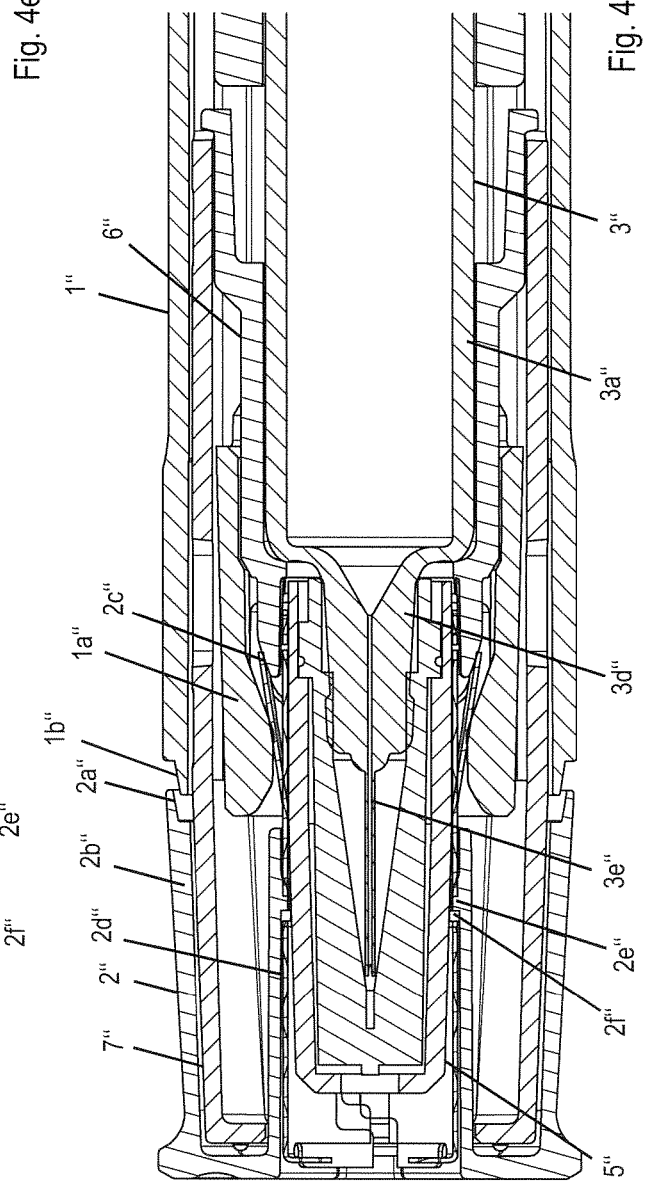

FIGS. 3*a*-3*d* show longitudinal sectional views of a distal part of a second embodiment of an injection device according to the invention, wherein the individual assembly steps for assembling a device cap (2') on this injection device can be seen. FIGS. 3*e* and 3*f* show longitudinal sectional views of the distal part of the second embodiment of the injection device, wherein the pulling off of the device cap (2') from the injection device can be seen. In multiple assembly steps, a product container holder (6') and a needle protection sleeve (7') are arranged in a housing (1') of the injection device. Alternatively, the housing (1') and the product container (6') can be formed integrally, in which case the step of inserting the product container holder (6') into the housing (1') can be omitted. Alternatively, it is possible that the injection device does not have a needle protection sleeve (7'), in which case the step of inserting the needle protection sleeve (7') into the housing (1') can be omitted. A blocking element (1*a'*) is provided on the housing (1') or on a part fixed relative to the housing (1'). The blocking element (1*a'*) has at least one first oblique face. The first oblique face protrudes inwardly. The first oblique face has an inclination. In addition, a device cap (2') is arranged at a distal end of the housing (1'). The device cap (2') comprises a sleeve (2*b'*), a remover element (2*d'*) and an engagement element (2*c'*). The sleeve (2*b'*) can comprise an inner sleeve and an outer sleeve. The sleeve (2*b'*), the remover element (2*d'*) and the engagement element (2*c'*) are axially fixedly connected to one another. The sleeve (2*b'*) partially surrounds the engagement element (2*c'*), more particularly the remover element (2*d'*) and the engagement element (2*c'*). The remover element (2*d'*) and the engagement element (2*c'*) are preferably integrally formed, while the sleeve (2*b'*) is a separate part. The remover element (2*d'*) and the engagement element (2*c'*) are preferably formed from a stamped-bent part. The remover element (2*d'*) is preferably axially fixedly connected via a protrusion/recess connection (2*e'*, 2*f*) to the sleeve (2*b'*). The engagement element (2*c'*) is preferably made from metal, particularly steel, particularly preferably stainless steel or spring steel. The engagement element (2*c'*) is made from a material that has a bending strength that allows a plastic and/or elastic deformation. The engagement element (2*c'*) can be deformed in such a manner that it becomes deformed, more particularly deformed radially outwardly or radially inwardly, or assumes an undeformed shape. The engagement element (2*c'*) can be deformed in such a manner that it becomes deformed, more particularly deformed radially outwardly or radially inwardly, or is or becomes undeformed. The engagement element (2*c'*) is hook-shaped. The hook-shaped engagement element (2*c'*) comprises a long and a short limb. The short limb of the hook-shaped engagement element (2*c'*) protrudes toward the interior of the injection device in the direction of the longitudinal axis (L) of the injection device. When the device cap (2') is being placed on the distal end of the housing (1'), the engagement element (2*c'*), more particularly the long limb of the hook-shaped engagement element (2*c'*), is not deformed. When the device cap (2') is placed on the injection device, the engagement element (2*c'*) moves axially relative to the blocking element (1*a'*) of the housing (1') in the proximal direction, and the engagement element (2*c'*) is not deformed, in particular not deformed plastically and/or elastically. An engagement member (2*a'*) provided on the sleeve (2*b'*) of the device cap (2') engages with a mating engagement member (1*b'*) arranged on the housing. To further assemble the injection device, an assembly tool (8'), more particularly a spreading mandrel (8'), is introduced into the injection device from the proximal end of the housing (1') of the injection device. The spreading mandrel (8') comprises one or more bending elements (8*a*) that can deform the engagement element (2*c'*), more particularly radially outwardly. The engagement element (2*c'*) of the device cap (2') is deformed parallel to the first oblique face of the blocking element (1*a'*) of the housing (1'), more particularly plastically and/or elastically deformed. In the process, the bending element (8*a*) of the spreading mandrel (8') is moved from the longitudinal axis (L) of the injection device transversely to the longitudinal axis (L) of the injection device and then again toward the longitudinal axis (L). The assembly tool (8'), more particularly the spreading mandrel (8'), is pulled out of the injection device. The subassembly consisting of at least the housing (1') and the device cap (2), wherein the device cap (2') comprises the engagement element (2*c'*), can optionally be delivered for further assembly to a different assembly area. A product container (3') can be inserted into the product container holder (6') or into the housing (1') of the injection device. Due to the radially outwardly deformed engagement element (2*c'*) of the device cap (2'), no or very small forces are exerted by the engagement element (2*c'*) of the device cap (2') on the needle protection cap (5') during insertion of the product container (3') having the needle protection cap (5'). An injection needle (3*e'*) arranged on the product container (3') is sealed off sterilely against the surroundings by the needle protection cap (5'). The product container (3'), prefilled with the product, is inserted into the housing (1') from a proximal end of the housing (1'). The product container (3') is pushed in the distal direction relative to the product container holder (6') or to the housing (1') until it reaches a distal end position. The engagement element (2*c'*) of the device cap (2') is in the spaced-apart position, in which the engagement element (2*c'*) is at a radial distance from the needle protection cap (5'), which is arranged on the product container (3'). Thereafter, a drive unit can be placed in the housing (1') of the injection device. The drive unit can be inserted from the proximal end of the housing (1') into the housing (1'). Alternatively, the drive unit can be frictionally and/or form fittingly connected and/or integrally bonded to the housing (1') of the injection device. This completes the assembly of the injection device. The injection device is in the delivery condition. To use the injection device, the device cap (2') is removed from the distal end of the housing (1') of the injection device. This releases the form-fitting connection between the sleeve (2*b'*) of the device cap (2'), more particularly the engagement member (2*a'*) of the sleeve (2*b'*), and the housing (1'), more particularly the mating engagement member (1*b'*) of the housing. The device cap (2') moves in the distal direction relative to the housing (1'). In this movement, the engagement element (2*c'*), more particularly the long limb of the hook-shaped engagement element (2*c'*) of the device cap (2'), slides over the first oblique face of the blocking element (1*a'*) of the injection device housing (1'). The engagement element (2*a'*) is deformed in such a manner that the engagement element (2*c'*) comes into engagement with the needle protection cap (5'). The engagement element (2*c'*) of the device cap (2') moves into the engagement position, in which the engagement element (2*c'*) engages with the needle protection cap (5'), wherein the engagement element (2*c'*) is deformed during removal of the device cap, more particularly plastically and/or elastically deformed. In the process, the engagement element (2*c'*) preferably achieves an undeformed or radially inwardly deformed shape. The engagement element (2c') is axially fixedly connected to the needle protection cap (5'). The engagement element (2c'), more particularly the short limb of the hook-shaped engagement element (2c'), engages with or bores into an outer surface of the needle protection cap (5'). The needle protection cap (5') is entrained by the device cap (2'), the needle protection cap (5') being removed from the product container (3') and held in the device cap (2'). The injection device can be used for administering the product.

FIGS. 4a-4f show longitudinal sectional views of a distal part of a third embodiment of an injection device according to the invention, wherein the individual assembly steps for assembling the device cap (2") on this injection device can be seen. FIGS. 4g and 4h show longitudinal sectional views of the distal part of the third embodiment of the injection device, wherein the removal of the device cap (2") from the injection device can be seen. Initially, a product container holder (6") and a needle protection sleeve (7") are inserted into a housing (1") of the injection device. In another embodiment of the invention, the housing (1") and the product container (6") can alternatively be formed integrally, in which case the step of inserting the product container holder (6") into the housing (1") can be omitted. In an additional embodiment, it is possible that the injection device does not have a needle protection sleeve (7"), in which case the step of inserting the needle protection sleeve (7") into the housing (1") can be omitted. A blocking element (1a") is arranged on a housing (1") or on a part fixedly connected to the housing (1"), wherein the blocking element (1a") has at least one first oblique face. The first oblique face of the blocking element (1a") protrudes inwardly. The first oblique face has an inclination. In another step, a device cap (2") is attached to a distal end of the housing (1"). The device cap (2") preferably has a sleeve (2b"), a remover element (2d") and an engagement element (2c"). The sleeve (2b"), the remover element (2d") and the engagement element (2c") are preferably axially fixedly connected to one another. Alternatively, the sleeve (2b"), the remover element (2d") and the engagement element (2c") can be formed integrally. The sleeve (2b") can partially surround the engagement element (2c"), more particularly the remover element (2d") and the engagement element (2c"). The remover element (2d") and the engagement element (2c") are preferably integrally formed, while the sleeve (2b") forms a separate part. The remover element (2d") and the engagement element (2c") are preferably formed from a stamped-bent part. The remover element (2d") is preferably axially fixedly connected via a protrusion/recess connection (2e", 2f) to the sleeve (2b"). The engagement element (2c") is preferably made from metal, particularly steel, particularly preferably stainless steel or spring steel. The engagement element (2c") is formed from a material that has a bending strength that allows a plastic and/or elastic deformation. The engagement element (2c") can be deformed in such a manner that it becomes deformed, more particularly deformed radially outwardly or radially inwardly, or assumes an undeformed shape. The engagement element (2c") can be deformed in such a manner that it becomes deformed, more particularly deformed radially outwardly or radially inwardly, or is or becomes undeformed. The engagement element (2c") can be designed in a hook shape. The hook-shaped engagement element (2c") has a long and a short limb. When the device cap (2") is attached to the distal end of the housing (1"), the engagement element (2c"), more particularly the long limb of the hook-shaped engagement element (2c"), is undeformed. When the device cap (2") is being placed on the distal end of the injection device, the engagement element (2c") moves axially relative to the blocking element (1a") of the housing (1") in the proximal direction, wherein the engagement element (2c") is not deformed, in particular not deformed plastically and/or elastically. At the end of the placement movement of the device cover (2"), an engagement member (2a") provided on the sleeve (2b") engages with a mating engagement member (1b") arranged on the housing. In an additional step, an assembly tool (8"), more particularly a spreading mandrel (8"), is introduced into the injection device from the proximal end of the housing (1") of the injection device. One or more bending elements of the spreading mandrel (8") deform the engagement element (2c"). The engagement element (2c") is deformed outwardly by the spreading mandrel (8") such that the engagement element (2c") deforms roughly parallel to the first oblique face of the blocking element (1a") of the housing (1"), more particularly plastically and/or elastically. In the process, the bending element of the spreading mandrel (8") is moved from the longitudinal axis (L) of the injection device transversely to the longitudinal axis (L) of the injection device and then again toward the longitudinal axis (L). After the plastic and/or elastic deformation of the engagement element (2c") of the device cap (2"), the spreading mandrel (8") is guided out of the injection device. Especially preferably, the product container (6") can be moved in the distal direction relative to the housing (1") before or after removal of the assembly tool (8"), more particularly the spreading mandrel (8"), in such a manner that the deformed, more particularly plastically and/or elastically deformed, engagement element (2c"), more particularly the long limb of the hook-shaped engagement element (2c") of the device cover (2") comes to a stop over a distal end of the product container (6"). The outwardly deformed engagement element (2c"), more particularly the elastically and/or plastically radially outwardly deformed long limb and/or the short limb of the engagement element (2c"), is supported on the distal end of the product container holder (6"). This support is used so that a premature engagement between the engagement element (2c") and the needle protection cap (5") does not occur. The distal end of the product container holder (6") can hold the engagement element (2c") in the deformed shape. The subassembly comprising at least the housing (1") and the device cap (2") can optionally be delivered for further assembly to a different assembly area. A product container (3"), prefilled with the product, can be inserted into the product container holder (6") or into the housing (1") of the injection device. Due to the radially outwardly deformed engagement element (2c") of the device cap (2"), no or very small forces are exerted by the engagement element (2c") of the device cap (2") on the needle protection cap (5") during insertion of the product container (3") having the needle protection cap (5"). The injection needle (3e") of the product container (3") is sealed off sterilely against the surroundings by the needle protection cap (5"). The product container (3") is inserted from a proximal end of the housing (1") into the housing (1"), wherein the product container (3") is displaced in the distal direction relative to the product container holder (6") or the housing (1") until it reaches a distal end position. The engagement element (2c") of the device cap (2") is in the spaced-apart position, in which the engagement element (2c") is at a radial distance from the needle protection cap (5"). In an additional step, the drive unit can be placed in the housing (1") of the injection device. The drive unit can likewise be inserted from the proximal end of the housing (1") into the housing (1"). In other embodiments, the drive unit can be frictionally and/or form fittingly connected and/or integrally bonded to the housing (1") of the injection device. The injection device is in the delivery condition. To use the injection device, the device cap (2") is removed from the distal end of the housing (1") of the injection device. This releases the form-fitting connection between the sleeve (2b") of the device cap (2") and the housing (1"). The device cap (2") moves in the distal direction relative to the housing (1"). In this axial movement or combined axial-rotational movement, the engagement element (2c"), more particularly the long limb of the hook-shaped engagement element (2c") of the device cap (2"), slides over the first oblique face of the blocking element (1a") of the injection device housing (1"). The engagement element (2c") is deformed in such a manner that the engagement element (2c") comes into engagement with the needle protection cap (5"). Alternatively, the engagement element (2c") deforms into the undeformed shape without action by the blocking element (1a"). The engagement element (2c") of the device cap (2") moves into the engagement position, in which the engagement element (2c") engages with the needle protection cap (5"), wherein the engagement element (2c") is deformed during removal of the device cap (2"). In the process, the engagement element (2c") preferably achieves an undeformed or radially inwardly deformed shape. The engagement element (2c") is axially fixedly connected to the needle protection cap (5"). The engagement element (2c"), more particularly the short limb of the hook-shaped engagement element (2c"), engages with or bores into an outer surface of the needle protection cap (5"). The needle protection cap (5") is entrained by the device cap (2"). The injection device can be used for administering the product.

FIGS. 5a-5c show longitudinal sectional views of a distal part of a fourth embodiment of an injection device according to the invention, wherein the individual assembly steps for assembling the device cap on this injection device can be seen. FIGS. 5d and 5e show longitudinal sectional views of the distal part of the fourth embodiment of the injection device, wherein the pulling off of the device cap (2''') from the injection device can be seen. In one step, the housing (1'''), which has the product container holder (6''') and a needle protection sleeve (7'''), is prepared. Alternatively, the housing (1''') and the product container holder (6''') can be formed integrally. In an additional embodiment, it is possible for the injector device not to comprise a needle protection sleeve (7'''), while at least one housing (1''') of the injector device is provided. A blocking element (1a''') is provided on the housing (1''') or on a part fixed relative to the housing (1'''). The blocking element (1a''') has at least one first and one second oblique face. The first and the second oblique faces protrude inwardly. The first and the second oblique faces each have an inclination. The first and the second oblique faces are inclined relative to one another. In addition, a device cap (2''') is provided. The device cap (2''') comprises a sleeve (2b'''), a remover element (2d''') and an engagement element (2c'''). The sleeve (2b'''), the remover element (2d''') and the engagement element (2c''') are preferably axially fixedly connected to one another. The sleeve (2b''') partially surrounds the engagement element (2c'''), more particularly the remover element (2d''') and the engagement element (2c'''). The remover element (2d''') and the engagement element (2c''') are preferably integrally formed, while the sleeve (2b''') forms a separate part. The remover element (2d''') and the engagement element (2c''') are preferably formed from a stamped-bent part. The remover element (2d''') is preferably axially fixedly connected via a protrusion/recess connection (2e''', 2f''') to the sleeve (2b'''). The engagement element (2c''') or the stamped-bent part is preferably made from metal, particularly steel, particularly preferably stainless steel or spring steel. The engagement element (2c''') or the stamped-bent part is made from a material that has a bending strength that allows a plastic and/or elastic deformation. The engagement element (2c''') can be deformed in such a manner that it becomes deformed, more particularly deformed radially outwardly or radially inwardly, or assumes an undeformed shape. The engagement element (2c''') can be deformed in such a manner that it becomes deformed, more particularly deformed radially outwardly or radially inwardly, or is or becomes undeformed. The engagement element (2c''') can be designed in a hook shape. The device cap (2''') is placed on the distal end of the housing (1'''), wherein the engagement element (2c'''), more particularly the long limb of the hook-shaped engagement element (2c'''), is undeformed. When the device cap (2''') is being placed on the distal end of the injection device, the engagement element (2c''') is moved in the proximal direction relative to the blocking element (1a''') of the housing (1'''), wherein the engagement element (2c'''), in particular the long limb of the hook-shaped engagement element (2c'''), is deformed radially inwardly, in particular deformed plastically and/or elastically radially inwardly. When the engagement element (2c''') reaches a position that is proximally offset relative to the blocking element (1a''') of the housing (1'''), the engagement element (2c''') reassumes its undeformed shape. At the same time, or when the movement is continued, an engagement member (2a''') provided on the sleeve (2b''') or the device cap (2c''') engages with a mating engagement member (1b''') and forms a releasable connection. The subassembly consisting of at least the housing (1''') and the device cap (2'''), wherein the device cap (2''') comprises the engagement element (2c'''), can optionally be delivered for further assembly to a different assembly area. A product container (3'''), prefilled with the product, can be inserted into the product container holder (6''') or into the housing (1''') of the injection device. Due to the undeformed engagement element (2c''') of the device cap (2'''), no or very small forces are exerted by the engagement element (2c''') of the device cap (2''') on the needle protection cap (5''') during insertion of the product container (3''') with the needle protection cap (5'''). An injection needle (3e''') provided on the product container (3''') is sealed off sterilely against the surroundings by the needle protection cap (5'''). The product container (3'''), prefilled with the product, is inserted into the housing (1''') from a proximal end of the housing (1'''). The product container (3''') is displaced in the distal direction relative to the product container holder (6''') or the housing (1''') until it reaches a distal end position. The engagement element (2c''') of the device cap (2''') is in the spaced-apart position, in which the engagement element (2c''') is at a radial distance from the needle protection cap (5'''). A drive unit can be inserted into the housing (1''') of the injection device with an additional step. The drive unit can be inserted from the proximal end of the housing (1''') into the housing (1'''). Alternatively, the drive unit can be frictionally and/or form fittingly connected and/or integrally bonded to the housing (1''') of the injection device. This completes the assembly of the injection device. The injection device is in the delivery condition. To use the injection device, the device cap (2''') is removed from the distal end of the housing (1''') of the injection device. This releases the form-fitting connection between the sleeve (2b''') of the device cap (2''') and the housing (1'''). The device cap (2''') moves in the distal direction relative to the housing (1'''). In this movement, the engagement element (2c'''), more particularly the long limb of the hook-shaped engagement element (2c''') of the device cap (2'''), slides over the first oblique face of the blocking element (1a''') of the injection device housing (1'''). The engagement element (2a''') is deformed, in particular elastically and/or plastically, in such a manner that the engagement element (2c''') comes into engagement with the needle protection cap (5'''). The engagement element (2c''') of the device cap (2''') moves into the engagement position, in which the engagement element (2c''') engages with the needle protection cap (5'''), wherein the engagement element (2c''') is deformed during removal of the device cap. The engagement element (2c''') deforms, more particularly plastically and/or elastically radially inwardly. The engagement element (2c''') preferably further comprises one or more fastening elements, wherein the fastening element is designed such that it can enter into a fixed, more particularly axially and radially fixed, connection to a needle protection cap (5'''), more particularly an outer surface of the needle protection cap (5'''). The needle protection cap (5''') is consequently entrained by the device cap (2''') during the removal movement of the device cap (2'''). The injection device can be used for administering the product.

Figure 6A:
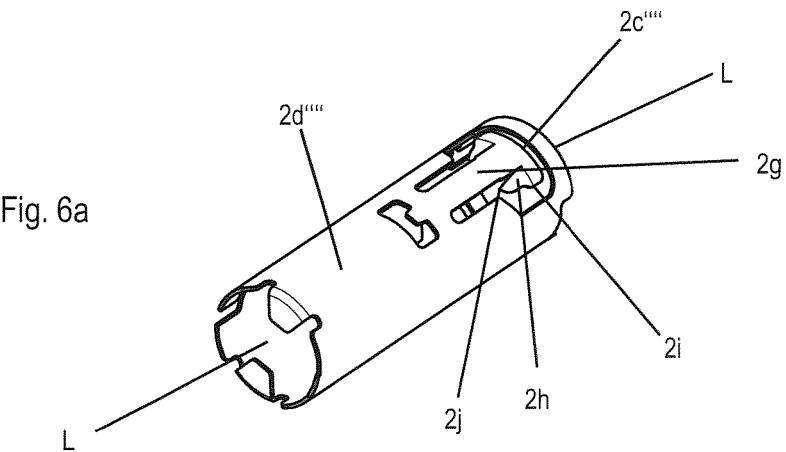
FIG. 6a shows a perspective view of a first embodiment of an engagement element (2c'''') having a longitudinal axis (L), wherein a remover element (2d'''') and the engagement element (2c'''') can be seen, and the engagement element (2c'''') is undeformed.
Figure 6B:
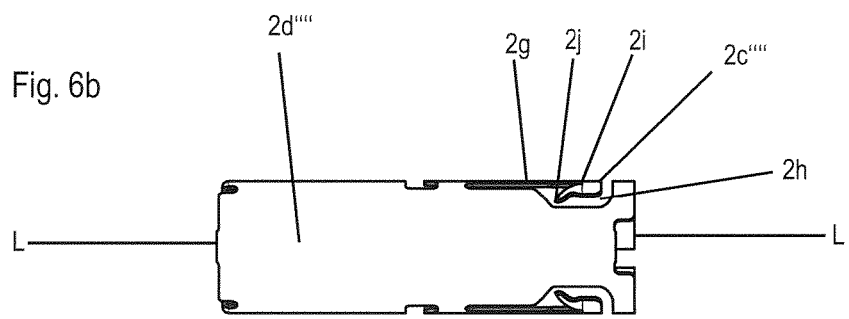
Figure 6C:
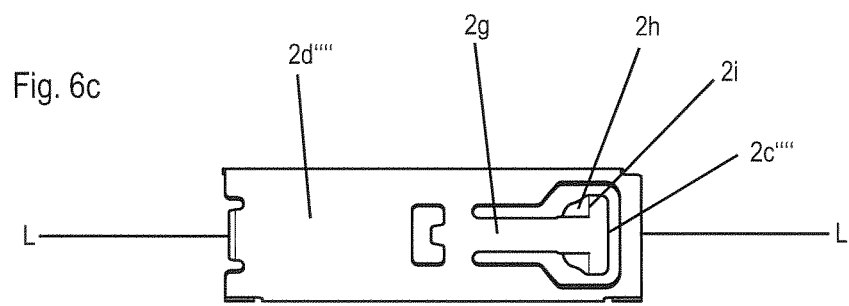
FIG. 6c shows a perspective view of the first embodiment of the engagement element (2c'''') according to FIG. 6b, wherein the view is rotated by 90° relative to the view of FIG. 6b.

FIG. 6a shows a perspective view of a first embodiment of an engagement element (2c'''') having a longitudinal axis (L), wherein a remover element (2d'''') and the engagement element (2c'''') are visible and the engagement element (2c'''') is undeformed. FIG. 6b additionally shows a perspective view along the longitudinal axis (L) of the first embodiment of the engagement element (2c'''') according to FIG. 6a. In addition, FIG. 6c shows a perspective view of the first embodiment of the engagement element (2c'''') according to FIG. 6b, wherein the view is rotated by 90° relative to the view of FIG. 6b. The first embodiment of the engagement element (2c'''') can be used for all the previously mentioned embodiments of an injection device according to the invention and/or for all the previously mentioned methods, more particularly for assembling an injection device and/or preparing an injection device for administration of a product. The engagement element (2c'''') in this embodiment is axially fixedly connected to the remover element (2d''''), wherein the remover element (2d'''') is axially fixedly connected to a sleeve (not visible) of a cap (not visible), in particular snap-fit, glued, overmolded or interlocked. In alternative embodiments, the engagement element (2c'''') can be axially fixedly connected to a cap (not visible) or to a sleeve (not visible), wherein no remover element (2d'''') is provided. In this embodiment, the remover element (2c'''') is sleeve-like in shape. It is especially preferred that the remover element (2d'''') and the engagement element (2c'''') are formed from a stamped-bent part. The stamped-bent part is plastically and/or elastically deformable. The stamped-bent part is preferably made from metal, particularly steel, especially preferably stainless steel, more particularly stainless spring steel. The hook-shaped engagement element (2d'''') comprises a long limb (2g) and a short limb (2h). The long limb (2g) and the short limb (2h) of the engagement element are connected to one another. The long limb (2g) is designed to be undeformed. The long limb (2g) extends along the longitudinal axis (L). The short limb (2h) protrudes radially inwardly. The short limb (2h) is tooth-shaped or triangular or has an acute angle. The short limb (2h) preferably comprises straight sides (2i) and curved sides. The short limb (2h) preferably comprises two curved sides and one straight side (2i). A tip (2j) of the tooth-shaped or triangular or acute-angled short limb (2h) protrudes radially inwardly. The tip (2j) is preferably arranged opposite from the straight side (2i) of the short limb (2h). The tip (2j) of the tooth-shaped or triangular or acute-angled short limb (2h) is designed such that the tip (2j) can engage with a needle protection cover (not visible). The tip (2j) is preferably shaped like a claw. The long limb (2g) and the short limb (2h) of the engagement element (2c'''') are connected to one another in such a manner, in particular connected plastically and/or elastically distortedly to one another, that the short limb (2h) extends from the long limb (2g) radially inwardly at an angle, more particularly at an angle of less than 90°, transversely to the longitudinal axis (L). The long limb (2g) and the short limb (2h) of the engagement element (2c'''') are connected to one another in such a manner that the straight side (2i) of the tooth-shaped or triangular or acute-angled short limb (2h) is connected to the long limb (2g) at an angle, more particularly an angle of 90°, transverse to the longitudinal axis (L), and the tip (2j) of the short limb (2h) of the engagement element (2c'''') protrudes radially inwardly. The long limb (2g) has multiple, more particularly two, short limbs (2h), wherein the two short limbs (2h) are arranged in the circumferential direction around the longitudinal axis (L). The remover element (2d'''') further comprises multiple, more particularly two long limbs (2g), wherein the two long limbs (2g) are provided opposite one another on the remover element (4d'''') or, alternatively, on the device cap (not visible) or on the sleeve (not visible).

FIG. 7a shows a perspective view of the first embodiment of the engagement element (2c'''') with the longitudinal axis (L), wherein a remover element (2d'''') and the engagement element (2c'''') can be seen and the engagement element (2c'''') is deformed, more particularly deformed elastically and/or plastically radially outwardly. FIG. 7b shows a perspective view along the longitudinal axis (L) of the first embodiment of the engagement element (2c'''') according to FIG. 7a. FIG. 7c additionally shows a perspective view of the first embodiment of the engagement element (2c'''') according to FIG. 7b, wherein the view is rotated by 90° relative to the view of FIG. 7b. The long limb (2g) of the engagement element (2c'''') can be deformed at an angle transverse to the longitudinal axis (L). In this embodiment, the long limb (2g) of the engagement element (2c'''') can be deformed at an angle transverse to the longitudinal axis (L), more particularly at an angle of less than 90° transverse to the longitudinal axis (L), elastically and/or plastically radially outwardly. In an alternative embodiment, the long limb (2g) of the engagement element (2c'''') can be deformed elastically and/or plastically radially inwardly at an angle transverse to the longitudinal axis (L), more particularly at an angle of less than 90° transverse to the longitudinal axis (L). The short limb (2h) protrudes radially inwardly.

Figure 8A:
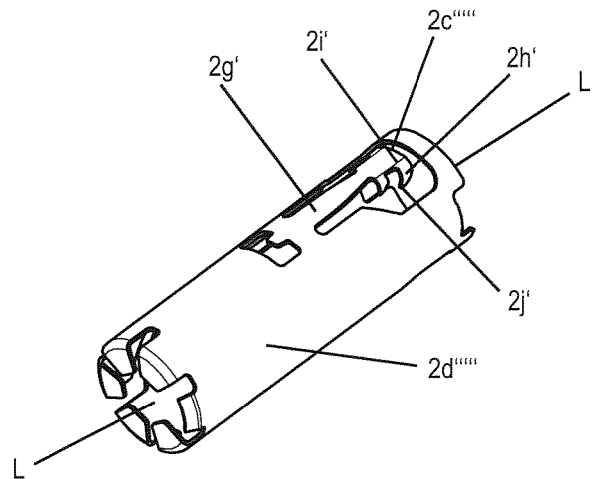
FIG. 8a shows a perspective view of a second embodiment of an engagement element (2c''''') having a longitudinal axis (L), wherein a remover element (2d''''') and the engagement element (2c''''') can be seen, and the engagement element (2c''''') is undeformed.
Figure 8B:
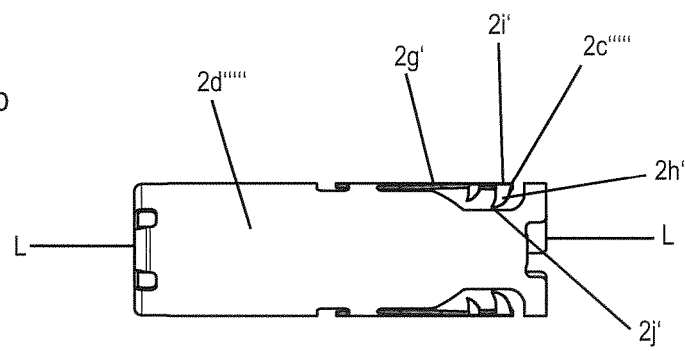
Figure 8C:
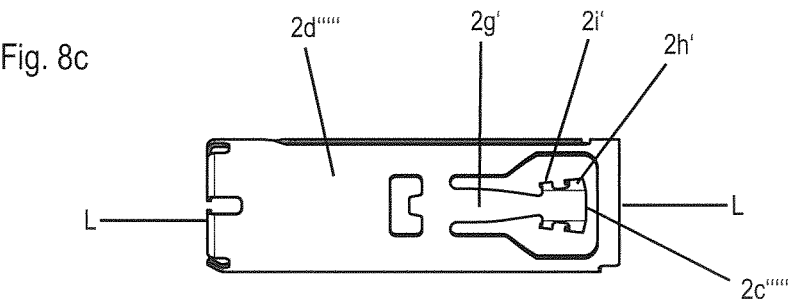
FIG. 8c shows a perspective view of the second embodiment of the engagement element (2c''''') according to FIG. 8b, wherein the view is rotated by 90° relative to the view of FIG. 8b.

FIG. 8a shows a perspective view of a second embodiment of an engagement element (2c'''''), which has a longitudinal axis (L), wherein a remover element (2d'''') and the engagement element (2c''''') are visible and the engagement element (2c''''') is undeformed. FIG. 8b shows a perspective view along the longitudinal axis (L) of the second embodiment of the engagement element (2c''''') according to FIG. 8a. FIG. 8c additionally shows a perspective view of the second embodiment of the engagement element (2c''''') according to FIG. 8b, wherein the view is rotated by 90° relative to the view of FIG. 8b. This second embodiment of the engagement element (2c''''') can be used for all the previously mentioned embodiments of an injection device according to the invention and/or can be used for all the previously mentioned methods, more particularly for assembling an injection device and/or preparing an injection device for administration of a product. The engagement element (2c''''') differs from the first embodiment of the engagement element (2c"") by the arrangement and/or the design of the long limb (2g') and the short limb (2h') of the engagement element (2c""). The long limb (2g') extends along the longitudinal axis (L). The long limb (2g') is designed to be undeformed. The short limb (2h') of the engagement element is preferably tooth-shaped or triangular or acute-angled. The tooth-shaped, triangular or acute-angled short limb (2h') has straight (2i') and curved sides. The short limb (2h') preferably has two curved sides and one straight side (2i'). A tip (2j') of the tooth-shaped or triangular or acute-angled short limb (2h') protrudes radially inwardly. The tip (2j') is preferably arranged opposite from the straight side (2i') of the short limb (2h'). The tip (2j') of the tooth-shaped or triangular or acute-angled short limb (2h') is designed such that the tip (2j') can engage with a needle protection cover (not visible). The tip (2j') is preferably shaped like a claw. The tip (2j') of the short limb (2h') protrudes radially inwardly. The long limb (2g') and the short limb (2h') of the engagement element (2c"") are connected to one another, in particular connected plastically and/or elastically to one another, and deformed in such a manner that the short limb (2h') extends from the long limb (2g') radially inwardly along the longitudinal axis (L) at an angle, more particularly at an angle to the longitudinal axis (L). The long limb (2g') and the short limb (2h') of the engagement element (2c"") can be connected to one another in such a manner that the straight side (2i') of the tooth-shaped or triangular or acute-angled short limb is connected to the long limb (2h') along the longitudinal axis (L), and the tip (2j') of the short limb of the engagement element protrudes radially inwardly. Multiple short limbs are provided on the long limb (2g'). The multiple, in particular two, short limbs (2g') are arranged in succession and along the longitudinal axis (L). In addition, multiple, in particular two, short limbs (2g') are arranged in the circumferential direction about the longitudinal axis (L). The multiple short limbs can be designed in different manners. The distances between the straight side (2i") and the tip (2j") of the tooth-shaped or triangular or acute-angled short limb (2h') are different, particularly the distances of the short limbs that are arranged in succession. In addition, the remover element (2d"") comprises multiple, in particular two, long limbs (2g'), the two long limbs (2g') being arranged opposite one another.

Figure 9A:
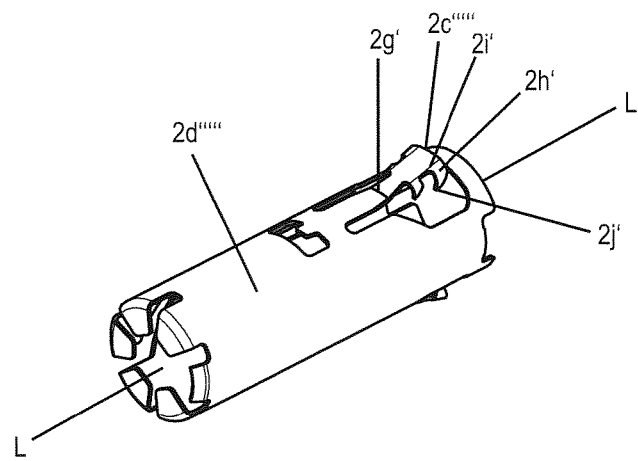
FIG. 9a shows a perspective view of the second embodiment of the engagement element (2c''''') having a longitudinal axis (L), wherein a remover element (2d''''') and the engagement element (2c''''') can be seen, and the engagement element (2c''''') is deformed, more particularly deformed radially outwardly.
Figure 9B:
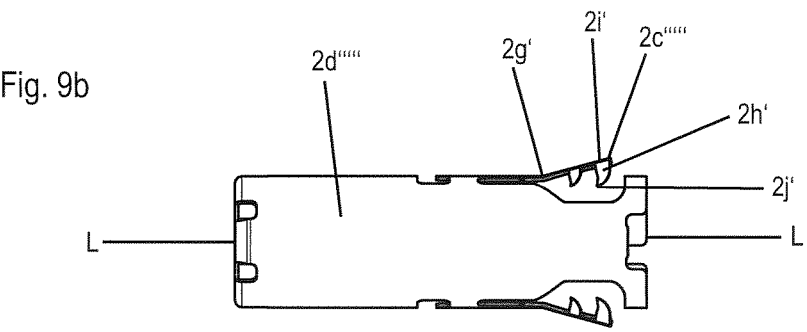
Figure 9C:
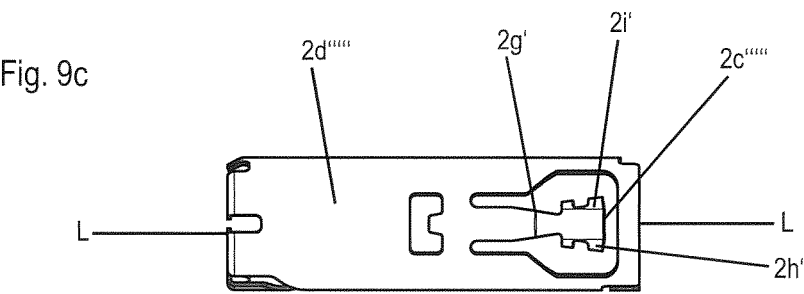
FIG. 9c shows a perspective view of the second embodiment of the engagement element (2c''''') according to FIG. 9b, wherein the view is rotated by 90° relative to the view of FIG. 9b.

FIG. 9a shows a perspective view of the second embodiment of the engagement element (2c"") with the longitudinal axis (L), wherein a remover element (2d"") and the engagement element (2c"") can be seen and the engagement element (2c"") is deformed, more particularly deformed elastically and plastically radially outwardly. Furthermore, FIG. 9b shows a perspective view along the longitudinal axis (L) of the first embodiment of the engagement element (2c"") according to FIG. 9a. FIG. 9c additionally shows a perspective view of the first embodiment of the engagement element (2c"") according to FIG. 9b, wherein the view is rotated by 90° relative to the view of FIG. 9b. The long limb (2g') of the engagement element (2c"") can be deformed at an angle transverse to the longitudinal axis (L). In this embodiment, the long limb (2g') of the engagement element (2c"") can be deformed radially at an angle transverse to the longitudinal axis (L), more particularly at an angle of less than 90° transverse to the longitudinal axis (L), elastically and/or plastically radially outwardly. In an alternative embodiment, the long limb (2g') of the engagement element (2c"") can be deformed elastically and/or plastically radially inwardly at an angle transverse to the longitudinal axis (L), more particularly at an angle of less than 90° transverse to the longitudinal axis (L). The short limb (2h') protrudes radially inwardly.

REFERENCE NUMBERS 1, 1', 1", 1'" Housing
1a, 1a', 1a", 1a'" Blocking element
1b, 1b', 1b", 1b'" Mating engagement member
2, 2', 2", 2'" Device cap
2a, 2a', 2a", 2a'" Engagement member
2b, 2b', 2b", 2b'" Sleeve
2c, 2c', 2c", 2c'", 2c"", 2c"" Engagement element
2d, 2d', 2d", 2d'", 2d"", 2d"" Remover element
2e, 2e', 2e", 2e'" Protrusion
2f, 2f, 2f", 2f'" [sic; 2f'"] Recess
2g, 2g' Long limb of the engagement element
2h, 2h' Short limb of the engagement element
2i, 2i' Straight side of the short limb
2j, 2j' Tip of the short limb
3, 3', 3", 3'" Product container
3a, 3a', 3a", 3a'" Product container portion
3b Piston
3c Flange
3d, 3d', 3d", 3d'" Needle holding portion
3e, 3e', 3e", 3e'" Injection needle
4 Piston rod
5, 5', 5", 5'" Needle protection cap
6, 6', 6", 6'" Product container holder
7, 7, 7", 7'" Needle protection sleeve
8, 8', 8" Assembly tool
8a Bending element
L Longitudinal axis

What is claimed is:

1. An injection device having a longitudinal axis, comprising:
   a housing for receiving a product container, wherein the product container comprises a fixedly connected injection needle, wherein a needle protection cap encloses the injection needle, seals the injection needle sterilely, and is releasably arranged on the product container; and
   a device cap releasably coupled to a distal end of the housing, wherein the device cap comprises an engagement element for removing the needle protection cap from the product container when the device cap is removed from the injection device,
   wherein the engagement element is deformable such that the engagement element can move from a spaced-apart position, in which the engagement element is at a radial distance from the needle protection cap, into an engagement position, in which the engagement element is engaged with the needle protection cap, wherein removal of the device cap causes the engagement element to be plastically deformed.

2. The injection device according to claim 1, wherein the engagement element is undeformed, deformed or deformed radially outwardly in the spaced-apart position.

3. The injection device according to claim 1, wherein the engagement element is undeformed, deformed or deformed radially inwardly in the engagement position.

4. The injection device according to claim 1, wherein the engagement element is hook-shaped.

5. The injection device according to claim 4, wherein the hook-shaped engagement element comprises a long limb and a short limb relative to the long limb, and wherein the long limb and the short limb are coupled to one another.

6. The injection device according to claim 5, wherein the long limb of the engagement element is deformable at an angle of less than 90°, transverse to the longitudinal axis.

7. The injection device according to claim 5, wherein the short limb of the engagement element protrudes radially inwardly.

8. The injection device according to claim 5, wherein the short limb of the engagement element is tooth-shaped, triangular or acute-angled.

9. The injection device according to claim 5, further comprising multiple short limbs provided on the long limb, wherein the multiple short limbs are arranged in a circumferential direction about the longitudinal axis, transverse to the longitudinal axis and/or along the longitudinal axis.

10. The injection device according to claim 1, wherein the engagement element is axially fixedly connected to the device cap.

11. The injection device according to claim 1, wherein the device cap further comprises a sleeve, wherein the sleeve at least partially surrounds the engagement element, and wherein the engagement element is axially fixedly connected to the sleeve.

12. The injection device according to claim 1, further comprising a blocking element provided on the housing or on a part fixedly connected to the housing, wherein the blocking element is configured to bring the engagement element into an engagement with the needle protection cap in the engagement position of the engagement element or maintains the engagement.

13. A method for assembling an injection device and/or preparing an injection device for the administration of a product, comprising the following steps:
    providing a housing for receiving a product container;
    providing a device cap releasably attached at a distal end of the housing, wherein the device cap comprises an engagement element for removal of a needle protection cap from the product container as the device cap is removed from the injection device;
    attaching the device cap at the distal end of the housing;
    providing a product container comprising a fixedly connected injection needle, wherein the needle protection cap encloses the injection needle to seal the needle sterilely against the surroundings, and is releasably arranged on the product container; and
    displacing or inserting the product container comprising the releasably connected needle protection cap into the housing in a distal direction along a longitudinal axis, wherein the engagement element is deformable, deformed or pre-deformed such that, during the displacement of the product container in the distal direction relative to the housing, the needle protection cap is at a radial distance from the engagement element; and
    causing the needle protection cap to be removed by causing the device cap to be removed, wherein removal of the device cap causes the engagement element to be plastically deformed, and the engagement element has a bending strength such that after removal of the device cap, the bending strength allows the engagement element to remain plastically deformed.

14. The method according to claim 13, wherein the engagement element engages with the needle protection cap as the device cap is removed from the injection device.

15. The method according to claim 14, wherein a blocking element is provided on the housing or a part fixedly connected to the housing and brings the engagement element into engagement with the needle protection cap.

16. The method according to claim 14, wherein the engagement element is undeformed, deformed or deformed radially outwardly before displacement of the product container relative to the housing.

17. The method according to claim 16, further comprising using an assembly tool to bring the engagement element into a spaced-apart position.

18. The method according to claim 14, further comprising inserting a needle protection sleeve into the housing, wherein the device cap is placed at a distal end of the needle protection sleeve.

* * * * *